(12) United States Patent
Bao et al.

(10) Patent No.: US 7,718,160 B2
(45) Date of Patent: May 18, 2010

(54) RADIOLABELED COMPOUNDS AND LIPOSOMES AND THEIR METHOD OF MAKING AND USING SAME

(75) Inventors: Ande Bao, San Antonio, TX (US); William T. Phillips, San Antonio, TX (US); Beth Goins, San Antonio, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 1312 days.

(21) Appl. No.: 10/518,872

(22) PCT Filed: May 22, 2003

(86) PCT No.: PCT/US03/16363

§ 371 (c)(1), (2), (4) Date: Jun. 17, 2005

(87) PCT Pub. No.: WO2004/004635

PCT Pub. Date: Jan. 15, 2004

(65) Prior Publication Data

US 2005/0222396 A1    Oct. 6, 2005

Related U.S. Application Data

(60) Provisional application No. 60/393,619, filed on Jul. 2, 2002.

(51) Int. Cl.
*A61K 51/00* (2006.01)
*A61M 36/14* (2006.01)
*C07F 5/00* (2006.01)
*C07F 13/00* (2006.01)

(52) U.S. Cl. .................. 424/1.65; 424/1.11; 424/1.21; 424/1.61; 534/11; 534/14

(58) Field of Classification Search ................ 424/1.11, 424/1.21, 1.65, 1.61; 534/11, 14
See application file for complete search history.

(56) References Cited

U.S. PATENT DOCUMENTS

| | | | |
|---|---|---|---|
| 4,310,505 A | 1/1982 | Baldeschwieler et al. .. | 424/1.21 |
| 4,776,991 A | 10/1988 | Farmer et al. ................. | 264/4.3 |
| 4,911,929 A | 3/1990 | Farmer et al. ................. | 264/4.3 |
| 5,013,556 A | 5/1991 | Woodle et al. ............... | 424/450 |
| 5,059,421 A | 10/1991 | Laughrey et al. ............ | 424/417 |
| 5,143,713 A | 9/1992 | Phillips et al. .............. | 424/1.21 |
| 5,158,760 A | 10/1992 | Phillips ........................ | 424/1.1 |
| 5,395,619 A | 3/1995 | Zalipsky et al. ............. | 424/450 |
| 5,589,189 A | 12/1996 | Moynihan et al. ........... | 424/450 |
| 5,665,380 A | 9/1997 | Wallach et al. ............... | 424/450 |
| 5,674,528 A | 10/1997 | Ogata et al. .................. | 424/450 |
| 5,676,971 A | 10/1997 | Yoshioka et al. ............. | 424/450 |
| 5,688,526 A | 11/1997 | Okamoto et al. ................ | 514/6 |
| 5,770,560 A | 6/1998 | Fischer et al. ................... | 514/6 |
| 5,814,601 A | 9/1998 | Winslow et al. ................ | 514/6 |
| 6,033,708 A | 3/2000 | Kwasiborski et al. ........ | 424/450 |
| 6,241,963 B1 | 6/2001 | Kung et al. | |
| 6,258,378 B1 | 7/2001 | Schneider et al. ............ | 424/450 |
| 6,294,191 B1 | 9/2001 | Meers et al. .................. | 424/450 |
| 6,316,024 B1 | 11/2001 | Allen et al. .................. | 424/450 |
| 6,316,028 B1 | 11/2001 | Wong et al. .................. | 424/473 |
| 6,320,017 B1 | 11/2001 | Ansell ......................... | 528/310 |
| 6,477,329 B2 | 11/2002 | Weng et al. .................. | 396/287 |
| 6,593,294 B1 | 7/2003 | Baru et al. | |
| 2002/0095108 A1 | 7/2002 | Tsuchida et al. ........... | 604/6.09 |
| 2002/0156062 A1 | 10/2002 | Boch et al. | |

FOREIGN PATENT DOCUMENTS

| | | |
|---|---|---|
| EP | 0 220 797 | 5/1987 |
| EP | 0 354 855 | 2/1990 |
| EP | 0 572 049 | 12/1993 |
| JP | 4005242 | 1/1992 |
| JP | 4300838 | 10/1992 |
| WO | WO 96/30054 A1 | 10/1996 |
| WO | WO 02/03959 | 1/2002 |

OTHER PUBLICATIONS

Permettis et al., J. Med. Chem., 1997, 90(160), p. 2539-46.*
Gupta, et al., Radiochimica Acta, 2001, 89(1), p. 43 (abstract).*
Chen et al., "Biodistribution, pharmacokinetics and imaging of Re-BMEDA-labeled pegylated liposomes after intraperitoneal injections in a C26 colon carcinoma ascites mouse model," Nuclear Medicine and Biology, 34:415-423 (2007).
Ahl et al., "Enhancement of the in vivo circulation lifetime of L-alpha-distearoylphosphatidylcholine liposomes: importance of liposomal aggregation versus complement opsonization." Biochim. Biophys. Acta. Oct. 23, 1997; 329(2):370-82.
Allen and Hansen, "Pharmacokinetics of stealth versus conventional liposomes: effect of dose." Biochim. Biophys. Acta. Sep. 30, 1991; 1068(2):122-41.
Allen et al., "Liposomes with prolonged circulation times: factors affecting uptake by reticuloendothelial and other tissues." Biochim. Biophys. Acta. 1989 981:27-35. (Abstract).
Awasthi et al., "Circulation and biodistribution profiles of long-circulating PEG-liposomes of various sizes in rabbits." Int. J. Pharm. 2003; 253:121-32.
Awasthi et al., "Kinetics of liposome-encapsulated hemoglobin after 25% hypovolemic exchange transfusion." International Journal of Pharmaceutics 283 (2004) 53-62.
Awasthi et al., "Neutral and Anionic Liposome-Encapsulated Hemoglobin: Effect of Postinserted Poly(ethylene glycol)-distearoylphosphatidylethanolamine on Distribution and Circulation Kinetics." The Journal of Pharmacology and Experimental Therapeutics, vol. 309, No. 1, JPET 309:241-248.
Banerjee et al. "Evolution of Tc-99m in Diagnostic Radiopharmaceuticals." Seminars in Nuclear Medicine, vol. XXXI, No. 4: 260-2777 (Oct. 2001).

(Continued)

*Primary Examiner*—Michael G Hartley
*Assistant Examiner*—Leah Schlientz
(74) *Attorney, Agent, or Firm*—Fulbright & Jaworski L.L.P.

(57) ABSTRACT

The invention, in one aspect, relates to radiolabeled compounds. The invention also relates to radiolabeled liposomes and methods of making and using thereof. The invention also relates to kits for preparing radiolabeled liposomes.

34 Claims, 17 Drawing Sheets

OTHER PUBLICATIONS

Blower et al. "Pentavalent rhenium-188 dimercaptosuccinic acid for targeted radiotherapy: synthesis and preliminary animal and human studies." Eur J Nucl Med. 25(6):613-21 (1998).

Bunjes et al. "Rhenium 188-labeled anti-CD66 (a, b, c, e) monoclonal antibody to intensify the conditioning regimen prior to stem cell transplantation for patients with high-risk acute myeloid leukemia or myelodysplastic syndrome: results of a phase I-II study." Blood. 98(3):565-72. (2001).

Carrion et al., "Preparation of long-circulating immunoliposomes using PEG-cholesterol conjugates: effect of the spacer arm between PEG and cholesterol on liposomal characteristics." Chem. Phys. Lipids. Nov. 2001; 113(1-2):97-110.

Chen et al. "Efficacy of Re-188-labelled sulphur colloid on prolongation of survival time in melanoma-bearing animals." Nuclear Medicine and Biology 28 (2001); 835-844.

Corbin et al. In "Preparation and Properties of Tripodal and Linear Tetradentate N,S-Donor Ligands and Their Complexes Containing the $MoO_2^{2+}$Core." Inorganica Chimica Acta, vol. 90, pp. 41-51 (1984).

Corvo et al., "Superoxide dismutase entrapped in long-circulating liposomes:-formulation design and therapeutic activity in rat adjuvant arthritis." Biochim. Biophys. Acta. Aug. 19, 2002; 1564(1):227-36.

Devine and Bradley, "The complement system in liposome clearance: Can complement deposition be inhibited?" Adv. Drug Deliv. Rev. Jun. 8, 1998; 32(1-2):19-29.

Drummond et al., "Optimizing liposomes for delivery of chemotherapeutic agents to solid tumors." Pharmacol. Rev. Dec. 1999; 51(4):691-743.

Ehrhardt et al. "Reactor-Produced Radionuclides at the University of Missouri Research Reactor." Appl. Radiat. 49(4):295-297 (1998).

Emfietzoglou et al. "An analytic dosimetry study for the use of radionucleotide-liposome conjugates in internal radiotherapy." J. Nucl. Med. 42(3):499-504 (2001).

Fillion et al., "Encapsulation of DNA in negatively charged liposomes and inhibition of bacterial gene expression with fluid liposome-encapsulated antisense oligonucleotides." Biochim. Biophys. Acta. Nov. 1, 2001; 1515(1):44-54.

Frank, Physiological Data of Laboratory Animals, in "Handbook of Laboratory Animal Science" (Melby EC, Jr. ed) pp. 23-64, CRC Press, Boca Raton, FL.

Frost & Sullivan, "Future of nuclear medicine, part 3: Assessment of the U.S. therapeutic radiopharmaceuticals market (2001-2020)." J Nuc Med. 39(7):14N-27N (1998).

Gabizon and Papahadjoulos, "The role of surface charge and hydrophilic groups on liposome clearance in vivo." Biochim. Biophys. Acta 1992; 1103:94-100.

Goins and Phillips, "The Use of scintigraphic imaging as a tool in the development of liposome formulation." Prog. Lipid Res. 2001; 40:95-123.

Goins et al., "Blood-pool imaging using technetium-99m-labeled liposomes." J. Nucl. Med. Aug. 1996; 37(8):1374-9.

Goins et al., "Physiological responses, organ distribution, and circulation kinetics in anesthetized rats after hypovolemic exchange transfusion with technetium-99m-labeled liposome-encapsulated hemoglobin." Shock. Aug. 1995; 4(2):121-30.

Goram and Richmond, "Pegylated liposomal doxorubicin: Tolerability and toxicity." Pharmacotherapy 2001; 21:751-63.

Grant N00014-00-1-0793 awarded by the Office of Naval Research.

Gregoriadis, "Fate of liposomes in vivo and its control: A historical perspective." in Stealth Liposomes (Lasic DD and Martin F eds),pp. 7-12, CRC Press, Boca Raton, FL (1995).

Hafeli et al. "A lipophilic complex with $^{186}Re/^{188}Re$ incorporated in liposomes suitable for radiotherapy." Nuc. Med. Biol. 18: 449-454 (1991).

Harashima et al., "Identification of proteins mediating cleatance of liposomes using a liver perfusion system." Adv. Drug Deliv. Rev. 1998; 32:61-79.

Hashimoto et al. "Rhenium Complexes Labeled with $^{186,188}Re$ for Nuclear Medicine." Curr. Chem. 176:275-291 (1996).

Hope et al., "Production of large unilamellar vesicles by a rapid extension procedure, characterization of size distribution, trapped volume & ability to maintain membrane potential." Biochim Biophys. Acta. 812:55-65, (1985).

Ishiwata et al. "Polyethyleneglycol derivatives of cholesterol reduces binding step of liposome uptake by murine macrophage-like cell line J774 and human heptoma cell line Hep62" Chem. Pharm. Bull. 1988, 46:1907-13.

Kim et al., "Pharmacodynamics of insulin in polyethylene glycol-coated liposomes." Int. J. Pharm. Mar. 25, 1999; 180(1):75-81.

Klibanov et al., "Activity of amphipathic poly(ethylene glycol) 5000 to prolong the circulation time of liposomes depends on the liposome size and is unfavorable for immunoliposome binding to target." Biochim. Biophys. Acta 1991; 1062:142-8.

Knapp et al. "Availability of Rhenium-188 from the Alumina-Based Tungsten-188/Rhenium-188 Generator for Preparation of Rhenium-188-Labeled Radiopharmaceuticals for Cancer Treatment." Anticancer Research 17:1783-1796 (1997).

Knapp et al. "Processing of Reactor-produced 188W for Fabrication of Clinical Scale Alumina-based 188W/188Re Generators." Appl. Radiat. Isot. 45(12):1123-1128 (1994).

Knapp et al. "The continuing important role of radionuclide generator systems for nuclear medicine." Eur. J. Nucl. Med. 21:151-165 (1994).

Kniess et al. "Cyclic voltametric investigations on oxorhenium(v) complexes of the "3+1" type" Forchungszent. Rossendorf FZR-122:136-9 (1996). Abstract.

Kostarelos and Emfietzoglou, "Liposomes as carriers of radionucleotides: from image to therapy." J. Liposome Res. 9(4):429-460 (1999).

Kostarelos et al. "Tissue dosimetry of liposome-radionuclide complexes for internal radiotherapy: toward lipsome-targeted therapeutic radiopharmaceuticals" Anticaner Res. 20:3339-46 (2000).

Lasic, "Liposomes." Science and Medicine, May/Jun. (1996) 34-43.

Lasic and Martin, eds., Stealth Liposomes. CRC Press, Boca Raton, FL (1995). Chapter 1.

Laverman et al., "Preclinical and clinical evidence for disappearance of long-circulating characterisitcs of polyethylene glycol liposomes at low lipid dose." J. Pharmacol. Exp. Ther. 2000; 293:996-1001.

Levchenko et al., "Liposome clearance in mice: the effect of a separate and combined presence of surface charge and polymer coating." Int. J. Pharm. Jun. 20, 2002; 240(1-2):95-102.

Li et al. "Rhenium-188 HEDP to treat painful bone metastases." Clin Nucl Med. 26(11):919-22. (2001).

Litzinger and Huang "Amphipathic poly(ethylene glycol) 5000-stabilized dioleoylphosphatidylethanolamine liposomes accumulate in spleen." Biochim Biophys Acta. 1127(3):249-54 (1992).

Liu et al., "Role of liposome size and RES blockade in controlling biodistribution and tumor uptake of GM1-containing liposomes." Biochim. Biophys. Acta 1992; 1104:95-101.

Maruyama et al., "Prolonged circulation time in vivo of large unilamellar liposomes composed of distearoyl phosphatidylcholine and cholesterol containing amphipathic poly(ethylene glycol)." Biochim. Biophys. Acta 1992; 1128:44-9.

Mastrostamatis et al. "Tridentate ligands containing the SNS donar atom set as a novel backbone or the development of technetium brain-imaging agents." J Med Chem. 37:3212-3218 (1994).

Matsuoka, "Determination of methemoglobin and carboxyhemoglobin in blood by rapid colorimetry." Biol. Pharm. Bull. Nov. 1997; 20(11):1208-11.

Maurer-Spurej-et al. "Factors influencing uptake and retention of amino-containing drugs in large unilamellar vesicles exhibiting transmembrane ph gradients." Biochimica Biophysica Acta 1416:1-10 (1999).

Mayer et al., "Uptake of antineoplastic agents into large unilamellar vesicles in response to a membrane potential." Biochim. Biophys. Acta. Jun. 27, 1985; 816(2):294-302.

Mayer et al., "Vesicles of variable sizes produced by a rapid extrusion procedure." Biochim Biophys Acta. Jun. 13, 1986; 858(1):161-8 (1986).

Mayhew et al. "High-pressure continuous-flow system for drug entrapment in liposomes." Methods Enzymol. 149:64-77 (1987).

McCready and Cornes, "The potential of intratumoural unsealed radioactive source therapy." Eur J Nuc Med. 28:567-569 (2001).
Mease et al. "Newer methods of labeling diagnostic agents with Tc-99m." Seminars in Nuclear Medicine, vol. XXXI, No. 4:278-285 (Oct. 2001).
Miller et al., "Liposome-cell interactions in vitro: effect of liposome surface charge on the binding and endocytosis of conventional and sterically stabilized liposomes." Biochemistry. Sep. 15, 1998; 37(37):12875-83.
Moreira et al., "Use of the post-insertion technique to insert peptide ligands into pre-formed stealth liposomes with retention of binding activity and cytotoxicity." Pharm. Res. 2002; 19(3):265-9.
New, in Liposomes : A Practical Approach, New (ed), Oxford University Press, NY, 33-104 (1990).
Nicholas et al., "Effect of grafted polyethylene glycol (PEG) on the size, encapsulation efficiency and permeability of vesicles." Biochim. Biophys. Acta. Jan. 15, 2000; 1463(1):167-78.
Oja et al., "Influence of dose on liposome clearance: critical role of blood proteins." Biochim. Biophys. Acta 1996; 1281:31-7.
Papadopoulos et al. "Syn-anti isomerism in a mixed-ligand oxorhenium complex ReO[SN(R)S][S]." Inorg Chem 35: 7377-7383 (1996).
Petty, Research Techniques in the Rats. Charles C. Thomas, Springfield, IL (1982).
Phillips and Goins in Handbook of targeted delivery of imaging agents. Chapter 10, CRC Press, Boca Raton, FL (1995).
Phillips et al. "A simple method for producing a technecium-99m-labeled liposome, which is stable in vivo." Nuc. Med Biol. 19:539-547 (1992).
Phillips et al. "Development of Liposome Encapsulated Hemaglobin (LEH) and Studies of Hemorrhagic Shock by Use of Imaging Studies with Oxygen-15 and Other Radiotracers.".
Phillips et al., "Polyethylene glycol-modified liposome-encapsulated hemoglobin: a long circulating red cell substitute." J. Pharmacol. Exp. Ther. Feb. 1999; 288(2):665-70.
Phillips, "Delivery of gamma-imaging agents by liposomes." Adv. Drug Deliv. Rev. 1999; 37:13-32.
Proctor, "Blood substitutes and experimental models of trauma." J Trauma. May 2003; 54(5 Suppl):S106-9.
Qaim, "Production of High Purity $^{94m}$Tc for Postitron Emission Tomography Studies." Nuclear Medicine & Biology, vol. 27, pp. 323-328, 2000.
Rabinovici et al., "Liposome-encapsulated hemoglobin: an oxygen-carrying fluid." Circ Shock. Sep. 1990; 32(1):1-17.
Reiss, "Oxygen carriers ("blood substitutes")—raison d'etre, chemistry, and some physiology." Chem Rev. Sep. 2001; 101(9):2797-920.
Roberts and Bratton, "Colloid volume expanders. Problems, pitfalls and possibilities." Drugs. May 1998; 55(5):612-30.
Rudolph, "Encapsulation of Hemoglobin in Liposomes," in Blood substitutes: Physiological Basis of Efficacy, Intaglietta M. ed., pp. 90-104, Birkhauser, Boston, 1995.
Sakai et al., "Physical properties of hemoglobin vesicles as red cell substitutes." Biotechnol. Prog. Jan.-Feb. 1996; 12(1):119-25.
Sakai et al., "Poly(ethylene glycol)-conjugation and deoxygenation enable long-term preservation of hemoglobin-vesicles as oxygen carriers in a liquid state." Bioconjug. Chem. May-Jun. 2000; 11(3):425-32.
Sakai et al., "Surface modification of hemoglobin vesicles with poly-(ethylene glycol) and effects on aggregation, viscosity, and blood flow during 90% exchange transfusion in anesthetized rats." Bioconjug Chem. Jan.-Feb. 1997; 8(1):23-30.
Semple et al. "Interactions of liposomes and lipid-based carrier systems with blood proteins: Relation to clearance behaviour in vivo." Adv. Drug Deliv. Rev. Jun. 8, 1998; 32(1-2):3-17.
Shimada et al., "Determination of incorporated amounts of poly(ethylene glycol)-derivatized lipids in liposomes for the physicochemical characterization of stealth liposomes." Int. J. Pharm. Aug. 10, 2000; 203(1-2):255-63.
Solanki et al. "Seven-hour stabilization of 99mTc-exametazime (HMPAO) for cerebral perfusion." Nucl Med Commun. 19:567-572 (1998).
Sou et al., "Poly(ethylene glycol)-modification of the phospholipid vesicles by using the spontaneous incorporation of poly(ethylene glycol)-lipid into the vesicles." Bioconjug Chem. May-Jun. 2000; 11(3):372-9.

Squires, "Artificial blood." Science. Feb. 8, 2002; 295(5557):1002-5.
Srivastava et al. "Recent advances in radionuclide therapy." Seminars In Nuclear Medicine, vol. XXXI, No. 4: 330-341, (Oct. 2001).
Sriwongsitanont and Ueno, "Physicochemical properties of PEG-grafted liposomes." Chem. Pharm. Bull. (Tokyo). Sep. 2002; 50(9):1238-44.
Stewart, "Colorimetric determination of phospholipids with ammonium ferrothiocyanate." Anal. Biochem. May 1, 1980; 104(1):10-4.
Storm et al., "Novel developments in liposomal delivery of peptides and proteins." J. Control Release 1995, 36:19-24.
Szebeni, "Complement Activation-Related Pseudoallergy Caused by Liposomes, Micellar Crriers of Intravenous Drugs, and Radiocontrast Agents." *Critical Reviews in Therapeutic Drug Carrier Systems*, 18(6):567-606 (2001).
Szebeni, "The interaction of liposomes with the complement system." Crit Rev Ther Drug Carrier Syst. 1998; 15(1):57-88.
Takeoka et al., "Layer-controlled hemoglobin vesicles by interaction of hemoglobin with a phospholipid assembly." Langmuir 1996; 12:1755-9.
Thakur et al., "Indium-LLL labeled platelets: studies on preparation and evaluation of in vitro and in vivo functions." Thromb. Res. Oct. 1976; 9(4):345-57.
Thompson, "Drug Bioscreening: Drug Evaluation Techniques in Pharmacology," VCH Publishers, New York, 1990; 321-339.
Tomita et al., "A simple spectrophotometric method for determination of met-hemoglobin in dilute solution." J. Nara. Med. Assoc. 1968; 19:1-6.
Torchilin and Papisov, "Why do polyethylene glycol-coated liposomes circulate so long?" J. Liposome Res. 1994; 4:725-739.
Uster et al., "Insertion of poly(ethylene glycol) derivatized phospholipid into pre-formed liposomes results in prolonged in vivo circulation time." FEBS Lett. May 20, 1996; 386(2-3):243-6.
Vertut-Doi et al., "Binding and uptake of liposomes containing a poly(ethylene glycol) derivative of cholesterol (stealth liposomes) by the macrophage cell line J774: influence of PEG content and its molecular weight." Biochim Biophys Acta. Jan. 12, 1996; 1278(1):19-28.
Volkert et al. "Technetium-99m chelates as radiopharmaceuticals." Curr. Chem. 176:125-148 (1996).
Walde and Ichikawa, "Enzymes inside lipid vesicles: preparation, reactivity and applications." Biomol. Eng. Oct. 31, 2001; 18(4):143-77.
Webb et al., "Comparison of different hydrophobic anchors conjugated to poly(ethylene glycol): effects on the pharmacokinetics of liposomal vincristine." Biochim Biophys Acta. Jul. 17, 1996; 1372(2):272-82.
Yuda et al., "Prolongation of liposome circulation time by various derivatives of polyethyleneglycols." Biol Pharm Bull. Oct. 1996; 19(10):1347-51.
International Search Report (ISR) and Written Opinion, International Application No. PCT/US2005/027880, filing date Aug. 27, 2004, Applicant: Board of Regents, The University of Texas System.
Bao et al., "99mTc/186Re/188re-liposome radiolabeling for nuclear imaging and targeted radionuclide therapy," *Technetium, Rhenium and other Metals in Chemistry and Nuclear Medicine*, 6(1):381-386, 2002.
International Search Report, issued in International Application No. PCT/US03/16363, mailed Apr. 26, 2004.
Office Communication, issued in Australian Patent Application No. 2003241598, dated Jan. 15, 2008.
Office Communication, issued in European Patent Application No. 03 731 347, dated Jun. 22, 2009.
Papadopoulos et al., "Study on the formation of mixed ligand oxorhenium and oxotechnetium complexes (SNS/S combination)," *Inorganica Chimica Acta*, 295:1-8, 1999.
Pelecanou et al., "Interaction of [ReO(SNS) (S)] and [99mTc0(SNS) (S)] mixed ligand complexes with gluthatione: isolation and characterization of the product," *Inorganica Chimica Acta*, 281:148-152, 1998.
Sabba-Dimopoulou et al., "Epidraseis tis methodou 99mTc-episimaseon liposomation stin biologiki simperifora tous," *Chemika Chronika, Genike Ekdose*, 58(12):661-664, 1996.
Supplementary European Search Report, issued in European Patent Application No. 03 73 1347, dated Dec. 16, 2008.

* cited by examiner

RADIOLABELED COMPOUNDS AND LIPOSOMES AND THEIR METHOD OF MAKING AND USING SAME

CROSS-REFERENCE TO RELATED APPLICATION

This application claims the benefit of U.S. Provisional Patent Application Ser. No. 60/393,619, filed on Jul. 2, 2002. This provisional patent application is herein incorporated by this reference is its entirety for all of its teachings.

BACKGROUND OF THE INVENTION

Liposomes are of considerable interest because of their value as carriers for diagnostic agents, particularly radiopharmaceuticals for tracer and imaging studies. There are many advantages of using liposomes as carriers of therapeutic radionuclides. Some advantages include (1) the biocompatibility of liposomes; (2) liposome particles of varying sizes with a uniform population size range can readily be achieved by using extrusion techniques; (3) the surface of liposomes can be modified with different kinds of functional groups; (4) the distribution of liposomes can be functional and microtargeted; and (5) the mechanism of radioisotope diffusion from liposomes can be monitored, which is helpful in delivering a uniform dose distribution in the tumor tissues.

Radionuclides have been widely used as a non-invasive method for studying the distribution of drugs in vivo. However, attempts at labeling liposomes with radionuclides as imaging agents have produced variable results. Many radionuclides weakly bind to liposomes, causing radionuclide leaching from the liposome and resulting in inaccurate biodistribution data. Furthermore, the entrapment of water-soluble radionuclides within the liposome during manufacturing is relatively inefficient.

Thus, what is lacking in the art is radiolabeled compounds that can be used to produce stable radiolabeled liposomes. The invention satisfies this need and provides compounds containing a radionuclide that can be used in the formation of stable, radiolabeled liposomes that contain high amounts of a radionuclide.

SUMMARY OF THE INVENTION

In accordance with the purposes of this invention, as embodied and broadly described herein, this invention, in one aspect, relates to radiolabeled compounds. The invention also relates to radiolabeled liposomes and methods of making and using them thereof. The invention also relates to kits for preparing radiolabeled liposomes.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification together with the description serve to explain the principles of the invention.

DETAILED DESCRIPTION

Figure 1A:
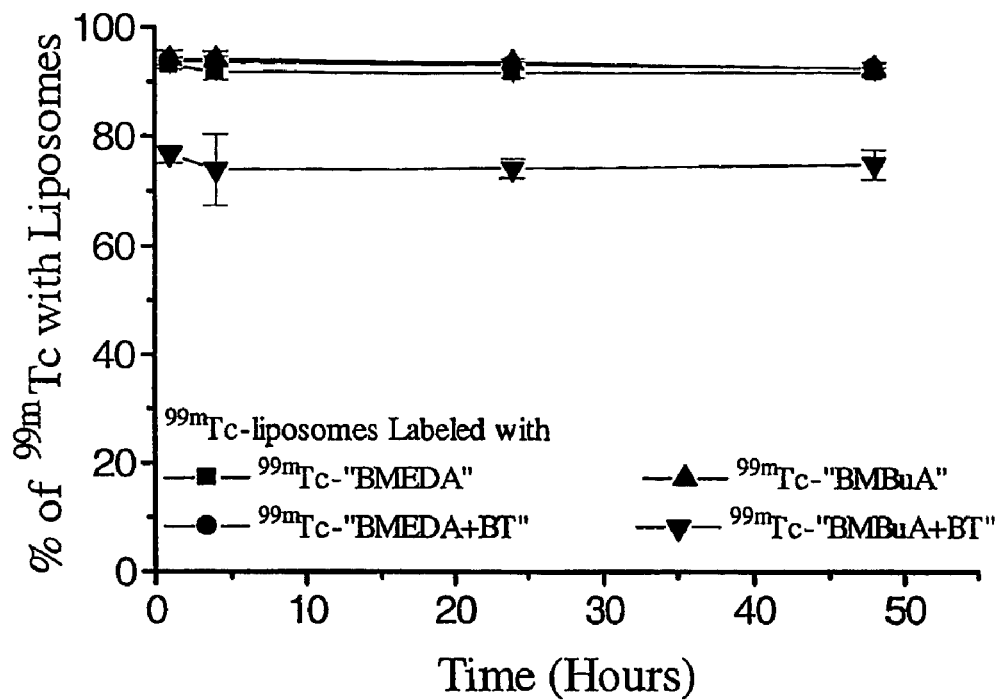
FIG. 1 shows the in vitro stability (average of three separate experiments) of $^{99m}$Tc-GSH liposomes labeled by using different kinds of $^{99m}$Tc-"SNS/S" complexes. Graph A shows the stability of $^{99m}$Tc-GSH liposomes at room temperature in PBS buffer. Graph B shows the stability of $^{99m}$Tc-GSH liposomes at 37° C. in 50% serum-PBS buffer.

The present invention may be understood more readily by reference to the following detailed description of preferred embodiments of the invention and the Examples included therein and to the Figures and their previous and following description.

Before the present compounds, compositions, and/or methods are disclosed and described, it is to be understood that this invention is not limited to specific synthetic methods, specific compositions, or to particular formulations, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about", it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Variables such as M, X, $R^1$, and $R^2$ used throughout the application are the same variables as previously defined unless stated to the contrary.

The term "alkyl group" is defined as a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like.

The term "alkenyl group" is defined as a hydrocarbon group of 2 to 24 carbon atoms and structural formula containing at least one carbon-carbon double bond.

The term "alkynyl group" is defined as a hydrocarbon group of 2 to 24 carbon atoms and a structural formula containing at least one carbon-carbon triple bond.

The term "aryl group" is defined as any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "cycloalkyl group" is defined as a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The term "aralkyl" is defined as an aryl group having an alkyl, alkynyl, or alkenyl group as defined above attached to the aromatic group. An example of an aralkyl group is a benzyl group.

The term "hydroxyl group" is represented by the formula —OH. The term "alkoxy group" is represented by the formula OR, where R can be an alkyl, alkenyl, alkynyl, aryl, aralkyl, cycloalkyl, halogenated alkyl, or heterocycloalkyl group described above.

The term "halogenated alkyl group" is defined as an alkyl having substituted for at least one hydrogen atom a halide group.

The term "amine group" is represented by the formula —NRR', where R and R' can be, independently, hydrogen or an alkyl, alkenyl, alkynyl, aryl, aralkyl, cycloalkyl, halogenated alkyl, or heterocycloalkyl group described above.

The term "amide group" is represented by the formula —C(O)NRR', where R and R' can be hydrogen, an alkyl, alkenyl, alkynyl, aryl, aralkyl, cycloalkyl, halogenated alkyl, or heterocycloalkyl group described above.

The term "ester" is represented by the formula —OC(O)R, where R can be an alkyl, alkenyl, alkynyl, aryl, aralkyl, cycloalkyl, halogenated alkyl, or heterocycloalkyl group described above.

The term "carbonate group" is represented by the formula —OC(O)OR, where R can be hydrogen, an alkyl, alkenyl, alkynyl, aryl, aralkyl, cycloalkyl, halogenated alkyl, or heterocycloalkyl group described above.

The term "carboxylic acid" is represented by the formula —C(O)OH.

The term "aldehyde" is represented by the formula —C(O)H.

The term "keto group" is represented by the formula —C(O)R, where R is an alkyl, alkenyl, alkynyl, aryl, aralkyl, cycloalkyl, halogenated alkyl, or heterocycloalkyl group described above.

The term "carbonyl group" is represented by the formula C=O.

The term "ether group" is represented by the formula R(O)R', where R and R' can be, independently, an alkyl, alkenyl, alkynyl, aryl, aralkyl, cycloalkyl, halogenated alkyl, or heterocycloalkyl group described above.

The term "halide" is defined as F, Cl, Br, or I.

The term "urethane" is represented by the formula —OC(O)NRR', where R and R' can be, independently, hydrogen, an alkyl, alkenyl, alkynyl, aryl, aralkyl, cycloalkyl, halogenated alkyl, or heterocycloalkyl group described above.

The term "thio group" is represented by the formula —SR, where R can be hydrogen, an alkyl, alkenyl, alkynyl, aryl, aralkyl, cycloalkyl, halogenated alkyl, alkoxy, or heterocycloalkyl group described above.

The term "silyl group" is represented by the formula —SiRR'R'', where R, R', and R'' can be, independently, hydrogen, an alky, alkenyl, alkynyl, aryl, aralkyl, cycloalkyl, halogenated alkyl, alkoxy, or heterocycloalkyl group described above.

The term "sulfo-oxo group" is represented by the formulas —S(O)$_2$R, —OS(O)$_2$R, or, —OS(O)$_2$OR, where R can be hydrogen, an alkyl, alkenyl, alkynyl, aryl, aralkyl, cycloalkyl, halogenated alkyl, or heterocycloalkyl group described above.

M, $R^1$, and $R^2$ can, independently, possess two or more of the groups listed above. For example, if $R^1$ is a straight chain alkyl group, one of the hydrogen atoms of the alkyl group can be substituted with a hydroxyl group, an alkoxy group, etc. Depending upon the groups that are selected, a first group may be incorporated within second group (e.g., an amino group can be incorporated within the ring of a cycloalkyl group) or, alternatively, the first group may be pendant (i.e., attached) to the second group (e.g., an amino group can be attached to the ring of a cycloalkyl group).

Reference will now be made in detail to the present preferred embodiments of the invention, examples of which are illustrated in the accompanying drawings. Wherever possible, the same reference numbers are used throughout the drawings to refer to the same or like parts.

Disclosed are compounds having the formula I wherein

M is a radionuclide;

X is oxygen, sulfur, or $NR^1$; and $R^1$ and $R^2$ are, independently, an alkyl group, a cycloalkyl group, a heterocycloalkyl group, an alkenyl group, an alkynyl group, an aryl group, a heteroaryl group, an aralkyl group, or a combination thereof, wherein $R^1$ and $R^2$ can be substituted with one or more groups comprising an alkoxy group, a hydroxy group, an amine group, a thio group, an amide, an ester, a carbonate group, a carboxylic acid, an aldehyde, a keto group, an ether group, a halide, a urethane group, a silyl group, or a sulfo-oxo group.

Compounds having the formula I contain a radionuclide represented by M. The term "radionuclide" is defined herein as any element that emits radiation. Examples of radiation that can be emitted from a radionuclide include, but are not limited to, α-emission, β-emission, γ-emission, x-ray-emission, conversion electron emission, or Auger electron emission. The radiation that is emitted from the radionuclide can be detected and measured using techniques known in the art (see Goins and Phillips "The use of scintigraphic imaging as a tool in the development of liposome formulations," *Progress in Lipid Research*, 40, pp. 95-123, 2001, which is incorporated by reference in its entirety). Examples of radionuclides useful in the invention are disclosed in "Srivastava et al in "Recent Advances in Radionuclide Therapy," *Seminars in Nuclear Medicine*, Vol. XXXI, No. 4, pp. 330-341, (October), 2001, which is incorporated by reference in its entirety. In one embodiment, M is technetium or rhenium. In another embodiment, M is $^{99m}$Tc, $^{186}$Re or $^{188}$Re.

The invention contemplates that $R^1$ and $R^2$ can be most any type of substituted or unsubstituted organic group. By varying the nature of $R^1$ and/or $R^2$, it is possible to modify the lipophilicity of formula I, which then affects the stability of the radiolabeled liposome. For example, when $R^1$ is a branched or straight alkyl group, the lipophilicity of the compound I increases. The lipophilicity of compounds of the invention is important with respect to liposome labeling, which will be discussed in detail below.

The presence of other functional groups in $R^1$ and/or $R^2$ can also influence the formation and the stability of the radiolabeled liposomes of the invention. In one embodiment, $R^1$ and/or $R^2$ contain groups that can be protonated. In one embodiment, X is $NR^1$ and $R^1$ is an alkyl group that contains at least one nitrogen atom. In another embodiment, $R^2$ has at least one nitrogen atom. In a further embodiment, $R^2$ contains one or two nitrogen atoms. In another embodiment, $R^2$ contains an unsubstituted or substituted aryl group. In another embodiment, $R^2$ has one nitrogen atom and one sulfur atom. In a further embodiment, $R^2$ has two nitrogen atoms and one sulfur atom.

In one embodiment, X is $NR^1$, $R^1$ is $CH_2CH_2NEt_2$, $R^2$ is $CH_2CH_2N(CH_2CH_2SH)(CH_2CH_2NEt_2)$, and M is $^{99m}$Tc, $^{186}$Re or $^{188}$Re. These compounds are referred to herein as M-"BMEDA" compounds. In another embodiment, X is $NR^1$, $R^1$ is $CH_2CH_2NEt_2$, $R^2$ is phenyl, and M is $^{99m}$Tc, $^{186}$Re or $^{188}$Re. These compounds are referred to herein as M-"BMEDA+BT" compounds.

In one embodiment, X is $NR^1$, $R^1$ is $CH_2CH_2CH_2CH_3$, $R^2$ is $CH_2CH_2N(CH_2CH_2SH)(CH_2CH_2CH_2CH_3)$, and M is $^{99m}$Tc, $^{186}$Re or $^{188}$Re. These compounds are referred to herein as M-"BMBuA" compounds. In another embodiment, X is $NR^1$, $R^1$ is $CH_2CH_2CH_2CH_3$, $R^2$ is phenyl, and M is $^{99m}$Tc, $^{186}$Re or $^{188}$Re. These compounds are referred to herein as M-"BMBuA+BT" compounds.

The compounds having the formula I contain a "SXS/S" ligand system, where the "SXS" notation represents the tridentate ligand backbone —$SCH_2CH_2XCH_2CH_2S$—, where X is oxygen, sulfur, or $NR^1$, and "/S" represents the $SR^2$ moiety in formula I. When the X represents an oxygen atom, the ligand system can be referred to herein as a "SOS/S" ligand system. When the X represents a sulfur atom, the ligand system can be referred to herein as the "SSS/S" ligand system. When the X represents a $NR^1$ group, the ligand system can be referred to herein as a "SNS/S" ligand system.

The compounds having the formula I can be made using techniques known in the art. The formation of formula I generally involves the addition of (1) a compound having the formula $HSCH_2CH_2XCH_2CH_2SH$ or the salt thereof (referred to herein as "the SXS compound"), (2) a thiol having the formula $HSR^2$ (referred to herein as "the S compound") or the salt thereof, and (3) a compound containing the radionuclide M. In one embodiment, the SXS compound and the S compound are the same compound. The SXS compounds can be prepared using techniques known in the art. In one embodiment, the procedure disclosed in Corbin et al. in "Preparation and Properties of Tripodal and Linear Tetradentate N,S-Donor Ligands and Their Complexes Containing the $MoO_2^{2+}$ Core," *Inorganica Chimica Acta*, vol. 90, pp. 41-51, 1984, which is incorporated by reference in its entirety, can be used to prepare the SXS compounds.

Compounds containing the radionuclide M can also be prepared by techniques known in the art. The methods for producing radionuclides disclosed in Banerjee et al., "Evolution of Tc-99m in Diagnostic Radiopharmaceuticals," *Seminars in Nuclear Medicine*, Vol. XXXI, No. 4:260-2777 (October 2001); Ehrhardt et al. "Reactor-produced Radionuclides at the University of Missouri Research Reactor," *Appl. Radiat.* 49(4):295-297 (1998); Hashimoto et al. "Rhenium Complexes Labeled with $^{186,188}$Re for Nuclear Medicine," *Curr. Chem.* 176:275-291 (1996); Knapp et al. "Availability of Rhenium-188 from the Alumina-Based Tungsten-188/Rhenium-188 Generator for Preparation of Rhenium-188-Labeled Radiopharmaceuticals for Cancer Treatment," *Anticancer Research* 17:1783-1796 (1997); Knapp et al. "The continuing important role of radionuclide generator systems for nuclear medicine," *Eur. J. Nucl. Med.* 21:151-1165 (1994); Knapp et al. "Processing of Reactor-produced $^{188}$W for Fabrication of Clinical Scale Alumina-based $^{188}$W/$^{188}$Re Generators," *Appl. Radiat. Isot.* 45(12):1123-1128 (1994); Mease et al. "Newer Methods of Labeling Diagnostic Agents with Tc-99m," *Seminars in Nuclear Medicine*, Vol. XXXLI, No. 4:278-285 (October 2001); and Volkert et al. "Technetium-99m Chelates as Radiopharmaceuticals," *Curr. Chem.* 176:125-148 (1996), which are incorporated by reference in their entireties, are useful in the invention.

The reaction between the SXS compound, the S compound, and the compound containing the radionuclide M to produce the compound having the formula I is generally conducted at pH of from about 1 to about 10 in water at from about 25° C. to about 100° C. for about 10 minutes to about 2 hours. After the reaction is complete, purification of the resulting radiolabeled compound having the formula I can be performed using techniques known in the art such as, for example, column chromatography.

Any of the radiolabeled compounds having the formula I can be used to produce a radiolabeled liposome. The term "radiolabeled liposome" as used herein refers to a liposome that has a compound having a radiolabeled compound of the invention incorporated or attached to the liposome. The term "liposome" referred to herein as any double membrane vesicle. The term "liposome" includes unilamellar and multilamellar liposomes.

The term "incorporated" as used herein refers to embedding a compound having the formula I in the double membrane of the liposome. Because the double membrane of liposomes is lipophilic, chemicals with high lipophilicity can be trapped within the double membrane of the liposome. As described above, it is possible to modify the lipophilicity of the radiolabeled compounds of the invention by varying the nature of $R^1$ and $R^2$. Thus, the present invention permits this mode of incorporation.

The term "incorporated" also refers to the entrapment of the radiolabeled compound within the inner volume or space of the liposomes. For this type of liposome labeling, a compound having the formula I can be encapsulated in the inner volume of the liposome. In this embodiment, once the compound is trapped within the inner volume of the liposome, the compound becomes more hydrophilic, which makes the compound harder to pass across the hydrophobic lipid double membrane of the liposome and escape. The presence of certain groups on $R^1$ and/or $R^2$ will determine the method of which the radiolabeled compound will be incorporated into the liposome. In one embodiment, if $R^1$ and/or $R^2$ possesses an amino group, then a pH gradient can be used to incorporate the radiolabeled compound into the liposomes. In another embodiment, the radiolabeled compound of the invention can react with a compound already present in the inner volume of the liposome to produce a new compound that is more hydrophilic. Each of these methods is described in greater detail below.

The term "attached" as used herein refers to the physical or chemical attachment of the radiolabeled compounds to the outer surface of liposome. The attachment can occur via any type of chemical bond such as, for example, a covalent, ionic, or hydrogen bond. In one embodiment, a radiolabeled compound having the formula I can be attached to the outer surface of the liposome via a covalent bond between either the SXS ligand or the S ligand and the liposome. In another embodiment, the SXS ligand can be covalently bonded to the outer surface of the liposome, then the radionuclide is coordinated to the SXS ligand. The method of attaching the radiolabeled compounds of the invention to the outer surface of the liposome will vary depending upon the radionuclide that is selected.

The invention contemplates the use of any liposome known in the art. The preparation of liposomes is well described in the literature (see, for example, Litzinger et al., *Biochim Biophys Acta*. 1127(3):249-254, 1992, New, in *Liposomes: A Practical Approach New* (ed), Oxford University Press, NY, 33-104, 1990, which is incorporated by reference in its entirety).

The materials that can be used to prepare the liposomes for use in the present invention include any of the materials or combinations thereof known to those skilled in the art as suitable for liposome preparation. In one embodiment, lipids may be used to prepare the liposomes. The lipids used may be of either natural or synthetic origin. The particular lipids are chosen to optimize the desired properties. Lipids which may be used to create liposomes include but are not limited to, lipids such as fatty acids, lysolipids, phosphatidylcholine with both saturated and unsaturated lipids including dioleoylphosphatidylcholine; dimyristoylphosphatidylcholine; dipentadecanoylphosphatidylcholine, dilauroylphosphatidylcholine, dipalmitoyl-phosphatidylcholine; distearoylphosphatidylcholine; phosphatidylethanolamines such as dioleoylphosphatidylethanolamine; phosphatidylserine; phosphatidylglycerol; phosphatidylinositol, sphingolipids such as sphingomyelin; glycolipids such as ganglioside GM1 and GM2; glucolipids; sulfatides; glycosphingolipids; phosphatidic acid, palmitic acid; stearic acid; arachidonic acid; oleic acid; lipids bearing polymers such as polyethyleneglycol, chitin, hyaluronic acid or polyvinylpyrrolidone; lipids bearing sulfonated mono-, di-, oligo- or polysaccharides; cholesterol or cholesterol analogues including, but not limited to, cholesterol sulfate and cholesterol hemisuccinate; tocopherol hemisuccinate; lipids with ether and ester-linked fatty acids; polymerized lipids, diacetyl phosphate; stearylamine; cardiolipin; phospholipids with short chain fatty acids of 6-8 carbons in length; synthetic phospholipids with asymmetric acyl chains (e.g., with one acyl chain of 6 carbons and another acyl chain of 12 carbons); 6-(5-cholesten-3-β-yloxy)-1-thio-β-D-galactopyranoside; digalactosyldiglyceride; 6-(5-cholesten-3-β-yloxy)hexyl-6-amino-6-deoxy-1-thio-β-D-galactopyranoside; 6-(5-cholesten-3-β-yloxy)hexyl-6-amino-6-deoxyl-1-thio-β-D-mannopyranoside; 12-(((7'-diethylaminocoumarin-3-yl)carbonyl)methyl-amino)octadecanoic acid; N-12-(((7'-diethylaminocoumarin-3-yl)carbonyl)methyl-amino)octadecanoyl-2-aminopalmitic acid; cholesteryl(4'-trimethylammonio)butanoate; N-succinyldioleoylphosphatidylethanolamine; 1,2-dioleoyl-sn-glycerol; 1,2-dipalmitoyl-sn-3-succinylglycerol; 1,3-dipalmitoyl-2-succinyl-glycerol; 1-hexadecyl-2-palmitoyl-glycerophosphoethanolamine; palmitoylhomocysteine, and/or combinations thereof.

In another embodiment, a variety of cationic lipids such as DOTMA, N-1-(2,3-dioleoyloxy)propyl-N,N,N-trimethylammonium chloride; DOTAP, 1,2-dioleoyloxy-3-trimethylammonio propane; DSTAP, 1,2-distearoyl-3-trimethyl-ammonium-propane; and DOTB, 1,2-dioleoyl-3-(4'-trimethylammonio)butanoyl-sn-glycerol may be used. In general the molar ratio of cationic lipid to non-cationic lipid in the liposome may be, for example, 1:1000, 1:100, preferably, between 2:1 to 1:10, more preferably in the range between 1:1 to 1:2.5 and most preferably 1.1 (ratio of mole amount cationic lipid to mole amount non-cationic lipid, e.g., DPPC). A wide variety of lipids may comprise the non-cationic lipid when cationic lipid is used to construct the liposomes. In one embodiment, the non-cationic lipid is dipalmitoylphosphatidylcholine, dipalmitoylphosphatidylethanolamine or dioleoylphosphatidylethanolamine. In lieu of cationic lipids as described above, lipids bearing cationic polymers such as polylysine or polyarginine may also be used to construct the liposomes and afford binding of a negatively charged therapeutic, such as genetic material, to the outside of the liposomes.

Other useful lipids or combinations thereof apparent to those skilled in the art are encompassed by the present invention. For example, carbohydrate-bearing lipids may be employed for in vivo targeting, as described in U.S. Pat. No. 4,310,505, the disclosure of which is hereby incorporated herein by reference in its entirety.

In one embodiment, the liposome is a phospholipid comprising DPPC and DSPC, preferably DSPC. In another embodiment, cholesterol can be included in the lipid formulation.

The size of the liposomes can be adjusted, if desired, by a variety of procedures including extrusion, filtration, sonication, homogenization, employing a laminar stream of a core of liquid introduced into an immiscible sheath of liquid, extrusion under pressure through pores of defined size, and similar methods, in order to modulate resultant liposomal biodistribution and clearance. The foregoing techniques, as well as others, are discussed, for example, in Mayer et al., *Biochim Biophys Acta*, 858:161-168, 1986; Hope et al., *Biochim Biophys Acta*, 812:55-65, 1985; Mayhew et al., *Methods in Enzymology*, 149:64-77, 1987. The disclosures of the foregoing publications are incorporated by reference herein, in their entirety.

The radiolabeled liposomes of the invention can be prepared using a number of techniques. In one embodiment, the radiolabeled compound having the formula I can be mixed with a liposome containing a drug. In one embodiment, the drug is incorporated within the liposome. Techniques for incorporating a drug into a liposome are known in the art. In one embodiment, the drug is a compound comprising at least one thiol group. The term "thiol group" is represented herein as —SH or the salt thereof. In another embodiment, the drug comprises glutathione, cysteine, N-acetyl cysteine, 2-mercaptosuccinic acid, 2,3-dimercaptosuccinic acid (DMSA), captopril or a combination thereof. The mixing step generally involves mixing the liposome, containing the drug with the compound having the formula I in a solvent. The mixing time and temperature will vary depending upon the nature of the liposome, the radiolabeled compound, and the drug incorporated within the liposome. In one embodiment, after the liposome and the compound having the formula I are mixed, the radiolabeled liposome is incubated at from 4° C. to 56° C. for 10 minutes to 24 hours.

In one embodiment, the drug reacts with the compound having the formula I. Not wishing to be bound by theory, it is believed that when the radiolabeled compound is incorporated into the liposome, the drug reacts with the radiolabeled compound by displacing —$SR^2$ to produce a radiolabeled drug. In one embodiment, when the drug possesses a thiol group (D-SH), the thiol group will react with M of the radiolabeled compound I to produce D-S-M and $HSR^2$. In this embodiment, once the drug reacts with the compounds having the formula I to produce a new radiolabeled compound, the new radiolabeled compound will not escape the liposome. In another embodiment, the invention also contemplates the incorporation of the radiolabeled compound I within the liposome, and the compound does not react with the drug. In a further embodiment, the radiolabeled compound can be attached to the outer surface of the liposome and the drug incorporated within the liposome.

In another embodiment, a pH gradient can be used to produce the radiolabeled liposome. In this embodiment, the pH of the inner volume of the liposome is different than pH of the outer surface of the liposome. The term "inner volume" is defined herein as the space within the membrane of the liposome. The term "inner space" also includes the space between the double membrane of the liposome. The term "outer surface" is defined herein as the outer surface of the membrane as well as the media the liposome is in (e.g., liquid, solid carrier, etc.).

In one embodiment, the pH of the inner volume of the liposome is acidic and the pH of the outer surface of the liposome is neutral, basic, or physiological pH. In this embodiment, lipid(s) is (are) hydrated or rehydrated with an acid in order to incorporate the acid within the liposome. In another embodiment, lipid(s) is (are) hydrated or rehydrated with a compound that contains at least one amine group or at least one carboxyl group. In the case of the amine group, the amine group is protonated to produce the corresponding ammonium salt, which is acidic. The carboxyl group can be the carboxylic acid or the salt thereof that can be protonated to produce the carboxylic acid. Examples of acids useful in this embodiment include, but are not limited to, ammonium sulfate, citric acid or tartaric acid. Once lipid(s) is (are) hydrated or rehydrated with the acid and the liposome is made, the liposome is washed with a solution that can remove any excess acid that may be on the outer surface of the liposome. In one embodiment, the liposome is washed with a buffer solution. In another embodiment, the pH of the inner volume of the liposome is from about 4 to about 7 and the pH of the outer surface is from about 6 to about 7. The procedure disclosed in Maurer-Spurej E et al. in "Factors Influencing Uptake and Retention of Amino-Containing Drugs in Large Unilamellar Vesicles Exhibiting Transmembrane pH Gradi-ents," *Biochimica et Biophysica Acta* 1416:1-10, 1999, can be used to prepared pH gradient liposomes useful in the invention.

In another embodiment, a chemotherapeutic agent, such as Doxorubicin, antibiotics or other treatment molecules can be incorporated or attached to the liposomes, which makes it possible for in vivo imaging of liposome encapsulated drug molecules or for the combined treatment with liposomes containing therapeutic radionuclides and /or drug molecules. Examples of chemotherapeutic agents include those disclosed in Maurer-Spurej E, Wong K F, Maurer N, Fenske D B, Cullis P R. "Factors influencing uptake and retention of amino-containing drugs in large unilamellar vesicles exhibiting transmembrane pH gradients" Biochimica et Biophysica Acta 1416: 1-10, 1999, which is incorporated by reference in its entirety.

Once the liposome having the pH gradient is produced, the liposome can be mixed with the compound having the formula I using techniques known in the art. The mixing step generally involves mixing the liposome with the compound having the formula I in a solvent. The mixing time and temperature will vary depending upon the nature of the liposome and the radiolabeled compound. Not wishing to be bound by theory, it is believed that in this embodiment, if the compound having the formula I possesses a group that can be protonated, it will facilitate the incorporation or attachment of the compound into the liposome. In one embodiment, $R^1$ and/or $R^2$ can possess an amino group that can be protonated. It is believed that once the compound having the formula I is protonated, the compound will remain incorporated within or attached to the liposome and not leach from the liposome. In one embodiment, after the pH gradient liposome is mixed with the compound having the formula I, the radiolabeled liposome is incubated at from about 4° C. to about 56° C. for about 10 minutes to about 24 hours.

In any of the methods for making the radiolabeled liposomes of the invention, an anti-oxidant can optionally be incorporated within the inner volume of liposome prior to radiolabeling. The procedures for incorporating an anti-oxidant into a liposome disclosed in U.S. Pat. Nos. 5,143,713 and 5,158,760, which are incorporated by reference in their entireties, can be used in this embodiment. In another embodiment, the radiolabeled liposome can be contacted with the ant-oxidant after radiolabeling. Examples of anti-oxidants include, but are not limited to ascorbic acid. The amount of anti-oxidant that can be incorporated into the liposome will vary depending upon the nature of the liposome, the radiolabeled compound, and the application of the radiolabeled liposome.

The use of compounds having the formula I for preparing radiolabeled liposomes as well as the methods for preparing the radiolabeled liposomes provides numerous advantages over the art. The radiolabeled liposomes are very stable. In other words, the radionuclide in the compound having the formula I does not escape the liposome once the compound is attached or incorporated within the liposome. Another advantage of the invention is that higher amounts of radionuclide can be attached or incorporated within the liposome. In one embodiment, the amount of radionuclide attached or incorporated within the liposome is from about 0.01 mCi to about 400 mCi per 50 mg of lipid used to prepare the liposome. In another embodiment, the lower limit of radionuclide that is attached or incorporated is 0.01, 0.05, 0.1, 0.2, 0.3, 0.5, 0.6, 0.7, 0.8, 0.9, 1.0, 2.0, 3.0, 4.0, 5.0, 6.0, 7.0, 8.0, 9.0, or 10 mCi, and the upper limit is 15, 17, 19, 21, 23, 25, 28, 30, 40, 50, 100, 150, 200, 250, 300, 350, or 400 mCi or more, where any lower limit can be used with any upper limit. These advantages are important with respect to the use of the radiolabeled compounds as imaging agents, which will be discussed in detail below.

The invention also contemplates a kit comprising the liposome containing the drug in one vial and the compound being used to make the formula I in a separate vial. In another embodiment, the invention contemplates a kit comprising the pH gradient liposome in one vial and the compound being used to make the formula I in a separate vial. In one embodiment, the contents of the vial containing the liposome are mixed with the contents of the vial containing the radiolabeled compound having the formula I to produce the radiolabeled liposome. In another embodiment, the kit comprises one vial that contains both the liposome and the radiolabeled compound, wherein the liposome and radiolabeled compound are separated from each other within the vial.

There are numerous applications for radiolabeled liposomes as imaging agents (see Goins and Phillips in "Handbook of Targeted Delivery of Imaging Agents," Chapter 10, CRC Press, 1995; and Srivastava and Dadachova "Recent Advances in Radionuclide Therapy," *Seminars in Nuclear Medicine*, vol. XXXI, No. 4, pp. 330-341, (October) 2001, which are incorporated by reference in their entireties). In one embodiment, the radiolabeled liposomes of the invention can be used in the imaging of tumors, infections, arthritis and inflammation, blood pools, lymph nodes, and myocardial infarction and ischemic tissues. The invention contemplates the use of the radiolabeled liposomes as imaging agents. By varying the size, charge, and composition of the liposome, it is possible to produce radiolabeled liposomes that are site specific. Additionally, varying the radionuclide M in formula I can affect the ability of the radiolabeled liposome to act as an imaging agent or diagnostic. In one embodiment, when the radiolabeled liposome is to be used as an imaging agent, the radionuclide is technetium.

The invention also contemplates the use of the radiolabeled liposomes of the invention to treat a disease in a subject. The selection of the radionuclide will determine if the radiolabeled liposome can treat a disease in a subject. In one embodiment, when the radionuclide is rhenium, the β-radiation that is emitted can kill certain cells. Additionally, the γ-radiation that is emitted from rhenium can be used as a diagnostic for determining the amount of rhenium that reaches the particular cells. Thus, the invention contemplates the use of radiolabeled liposomes simultaneously as an imaging agent and as a treatment of a disease. In one embodiment, the radiolabeled liposomes can be used to treat a subject having cancer.

The dosage or amount of radiolabeled liposome is large enough to produce the desired effect in which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician in the event of any counterindications. The dose, schedule of doses and route of administration may be varied, whether oral, nasal, vaginal, rectal, extraocular, intramuscular, intracutaneous, subcutaneous, intravenous, intratumoral, intrapleural, intraperitoneal or other practical routes of administration to avoid adverse reactions yet still achieve delivery.

The radiolabeled liposomes of the invention can be used therapeutically in combination with a pharmaceutically acceptable carrier. Pharmaceutical carriers are known to those skilled in the art. These most typically would be standard carriers for administration of compositions to humans and non-humans, including solutions such as sterile water, saline, and buffered solutions at physiological pH. In one embodiment, the compositions of the invention can be administered by injection including, but not limited to, intramuscular, subcutaneous, intraperitoneal, intratumoral or intravenous injection. Other compounds will be administered according to standard procedures used by those skilled in the art.

Radiolabeled liposomes intended for pharmaceutical delivery may be formulated in a pharmaceutical composition. Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

In one embodiment, the radiolabeled liposomes are administered to a subject comprising a human or an animal including, but not limited to a mouse, dog, cat, horse, bovine or ovine and the like, that is in need of alleviation or amelioration from a recognized medical condition. The radiolabeled liposomes may be administered to the subject in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed compositions can be administered intravenously, intraperitoneally, intramuscularly, subcutaneously, intratumoral, intracavity, or transdermally.

Preparations for parenteral administration include sterile aqueous or non-aqueous solutions, suspensions, and emulsions which may also contain buffers, diluents and other suitable additives. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration may include powders or granules, suspensions or solutions in water or non-aqueous media, capsules, sachets, or tablets. Thickeners, flavorings, diluents, emulsifiers, dispersing aids or binders may be desirable.

EXAMPLES

The following examples are put forth so as to provide those of ordinary skill in the art with a complete disclosure and description of how the compounds, compositions, and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Preparation of Liposomes Containing Cysteine or Glutathione

Liposomes were composed of distearoyl phosphatidylcholine (DSPC) (Avanti Polar Lipids, Pelham, Ala.); cholesterol (Chol) (Calbiochem, San Diego, Calif.); and alpha-tocopherol (Aldrich, Milwaukee, Wis.). All lipids were used without further purification. The lipids were mixed in chloroform at a total molar ratio of 54:44:2 (DSPC:Chol:α-tocopherol). Chloroform was then removed by rotary evaporation to form a lipid film. The lipid film was stored overnight in a vacuum desiccator to remove organic solvent. Samples were rehydrated with 300 mM sucrose (Sigma, St Louis, Mo.) in sterile water for injection and warmed to 55° C. for 15 minutes with periodic vortexing until all of the lipids were in suspension. The resultant multilamellar vesicles formed from rehydration were then frozen in liquid nitrogen and lyophilized.

The resultant dry sugar-lipid preparations were then rehydrated with either 200 mM reduced glutathione (GSH) (Sigma, St Louis, Mo.) or 200 mM cysteine (Sigma, St Louis, Mo.) in Dulbeccco's phosphate buffered saline pH 6.3 at a lipid concentration of 120 nM. The GSH-lipid suspension was warmed to 55° C. for 10 minutes. For some preparations, the suspension was allowed to cool to room temperature and then stored overnight in the refrigerator. The solutions were then diluted at a volume/volume ratio of 1 part lipid suspension to 2 parts Dulbecco's phosphate buffered saline containing 150 mM sucrose, and either 100 mM GSH or 100 mM cysteine. The diluted lipid suspensions were then extruded through a series (2 passes, 2µ; 2 passes, 400 nm; 2 passes, 200 nm; 5 passes, 100 nm) of polycarbonate filters (Lipex Extruder, Vancouver, Canada) at 55° C. The extruded lipid solution was then washed in Dulbecco's phosphate buffered saline containing 75 mM sucrose and centrifuged at 200,000×g for 45 minutes to remove unencapsulated sucrose and either unencapsulated GSH or cysteine, and to concentrate the liposome sample. The washing step was repeated 3 times. The final liposome pellet was resuspended in Dulbeccco's phosphate buffered saline pH 6.3 containing 300 mM sucrose at a lipid concentration of 120 mM and stored in the refrigerator at 4° C.

Synthesis of $^{186}$Re-"BMEDA"

This description is for labeling the liposomes with "BMEDA" because the $^{186}$Re-"BMEDA" complex produced the higher labeling efficiency and stability. "BMEDA" was synthesized using a modification of a procedure described by Corbin et al. in "Preparation and properties of tripodal and linear tetradentate N,S-donor ligands and their complexes containing the $MoO_2^{2+}$ core" *Inorganica Chimica Acta.* 1984; 90:41-51. First, a 0.17 M glucoheptonate-0.1 M acetate solution was prepared and the pH adjusted to 5.0 with 5 M NaOH. Next, the "BMEDA" solution was prepared by pipetting 4.5 mg of "BMEDA" (4.5 µl) to a new vial and adding 2.1 ml of the glucoheptonate-acetate solution. After flushing the "BMEDA"-glucoheptonate-acetate solution with $N_2$ gas for 20 min, the vial was sealed. The solution was stirred at 25° C. for 40 min. Next, 30 mg of $SnCl_2.2H_2O$ was dissolved by adding with 2 drops of concentrated HCl in a new vial and 2.0 ml of sterile water added.

To prepare the $^{186}$Re-"BMEDA" solution, 2.0 ml of "BMEDA" solution was transferred to a new vial and 280 µl of freshly prepared $SnCl_2.2H_2O$ was added. After flushing the "BMEDA" solution with $N_2$ gas, 50 mCi (1.85 GBq) of aluminum perrhenate $^{186}$Re—Al(ReO$_4$)$_3$ (~3.0 µg Re), purchased from the Missouri University Research Reactor (Columbia, Mo.), was added. The vial was sealed and heated in a 80° C. water bath for 1 hour. The labeling efficiency of the $^{186}$Re-"BMEDA" complex was checked by instant thin layer chromatography with either acetone or saline as the eluent.

$^{186}$Re-Liposome Labeling Protocol

For liposome labeling, the pH of the $^{186}$Re-"BMEDA" solution was adjusted to 7.0. Then, 1.0 ml of liposomes encapsulating cysteine was mixed with 0.7 ml of the $^{186}$Re-"BMEDA" solution, and incubated at 25° C. for 2 hours. More recent results have shown it is possible to achieve good labeling efficiencies after incubation at 37° C. for 1 hour. The labeling efficiency was determined from the $^{186}$Re-activity associated with the $^{186}$Re-liposomes before and after Sephadex G-25 column separation.

Synthesis of $^{99m}$Tc-"BMEDA+BT"

Although the labeling of liposomes with $^{99m}$Tc using "BMEDA" and "BMEDA+BT" are similar, the labeling protocol for "BMEDA+BT" is described because of the higher labeling efficiency and stability of "BMEDA+BT." First, $^{99m}$Tc-glucoheptonate was prepared by pipetting 1.0 ml of 10 mg/ml glucoheptonate into a vial containing 0.16 mg/ml degassed $SnCl_2$ solution. After mixing, 15 mCi (555 MBq) of $^{99m}$Tc-sodium pertechnetate (Amersham Medi-Physics, San Antonio, Tex.) in 2 ml of saline was added. The mixture was stirred at 25° C. for 20 minutes. The labeling efficiency of the $^{99m}$Tc-glucoheptonate was checked by instant thin layer chromatography (ITLC) eluted in methanol, paper chromatography eluted in methanol and paper chromatography eluted in saline.

Benzene thiol (BT) was purchased from Aldrich (Milwaukee, Wis.). The "BMEDA+BT" solution was prepared by pipetting 2.8 mg of "BMEDA" (2.5 µl) and 1.6 ng of BT (1.3 µl) to a new vial. Then, 5.0 ml of degassed water and 4 drops of 0.05 M NaOH was added. The solution was stirred at 25° C. for 40 minutes. After preparation, the "BMEDA+BT" solution was labeled with $^{99m}$Tc by adding 1.0 ml of "BMEDA+BT" solution to 0.65 ml of $^{99m}$Tc-glucoheptonate. After adjusting the pH to 8.0, the mixture was stirred at 25° C. for 25 min. The labeling efficiency of the $^{99m}$Tc-"BMEDA+BT" was determined using YTLC eluted in methanol, paper chromatography eluted in methanol and paper chromatography eluted in saline.

$^{99m}$Tc-Liposome Labeling Protocol

For liposome labeling, an aliquot (0.65 ml) of $^{99m}$Tc-"BMEDA+BT" was added to 1.0 ml of liposomes encapsulating cysteine and stirred at 25° C. for 2 hours. The labeling efficiency was determined from the $^{99m}$Tc-activity associated with the $^{99m}$Tc-liposomes before and after Sephadex G-25 column separation using a Radix dose calibrator.

In Vitro Stability of $^{99m}$Tc-Liposomes and $^{186}$Re-Liposomes

Figure 1B:
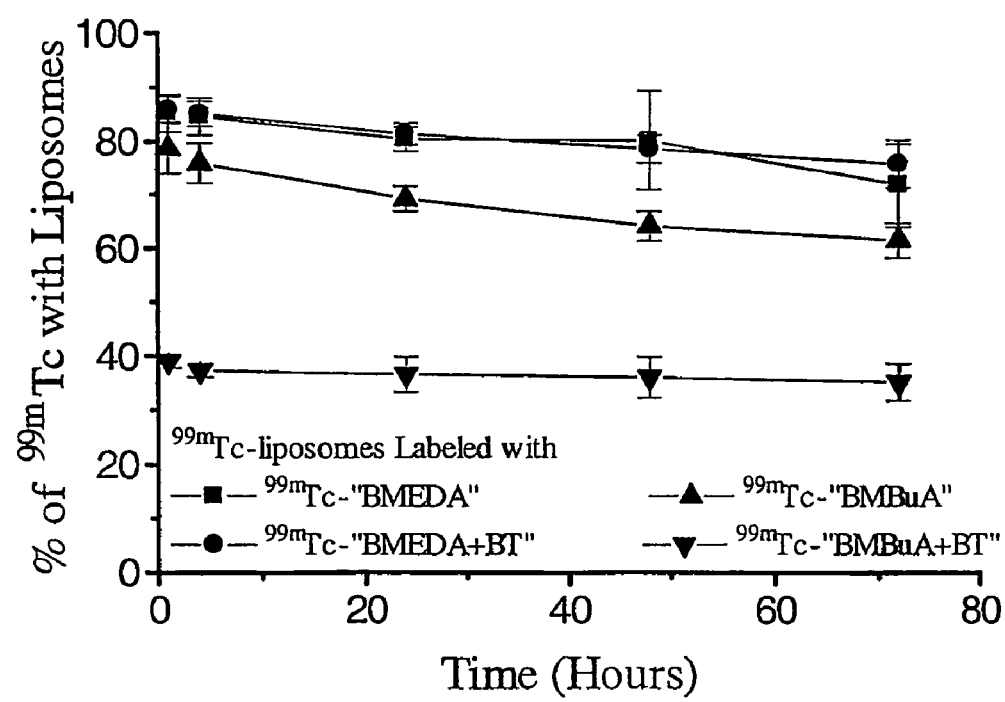

The in vitro stability results of $^{99m}$Tc-liposomes labeled with different $^{99m}$Tc-"SNS/S" complexes are shown in FIG. 1. When incubated with PBS buffer in the absence of serum at room temperature, $^{99m}$Tc-liposomes labeled with $^{99m}$Tc-"BMEDA," with $^{99m}$Tc-"BMEDA+BT" and with $^{99m}$Tc-"BMBuA" were stable, but with $^{99m}$Tc-"BMBuA+BT" were not so stable (FIG. 1A). When incubated in the presence of 50% serum with 50% PBS buffer at 37° C., only $^{99m}$Tc-liposomes labeled with $^{99m}$Tc-"BMEDA" and with $^{99m}$Tc-"BMEDA+BT" were stable, while $^{99m}$Tc-liposomes labeled with $^{99m}$Tc-"BMBuA" and with $^{99m}$Tc-"BMBuA+BT" were not as stable (FIG. 1B).

Figure 7A:
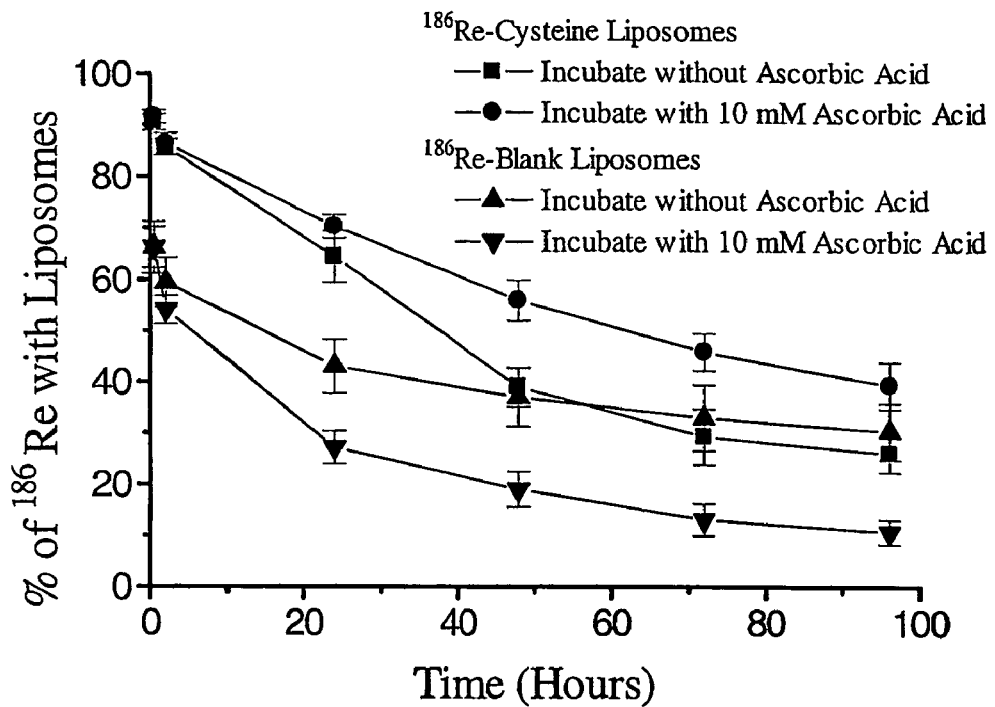
FIG. 7 shows the in vitro stability (average of three separate experiments) of $^{186}$Re-Cysteine liposomes and $^{186}$Re-Blank liposomes labeled with $^{186}$Re-"BMEDA" (Graph A) or with $^{186}$Re-"BMEDA+BT" (Graph B) in the presence or absence of 10 mM ascorbic acid in 50% serum-PBS buffer at 37° C.
Figure 7B:
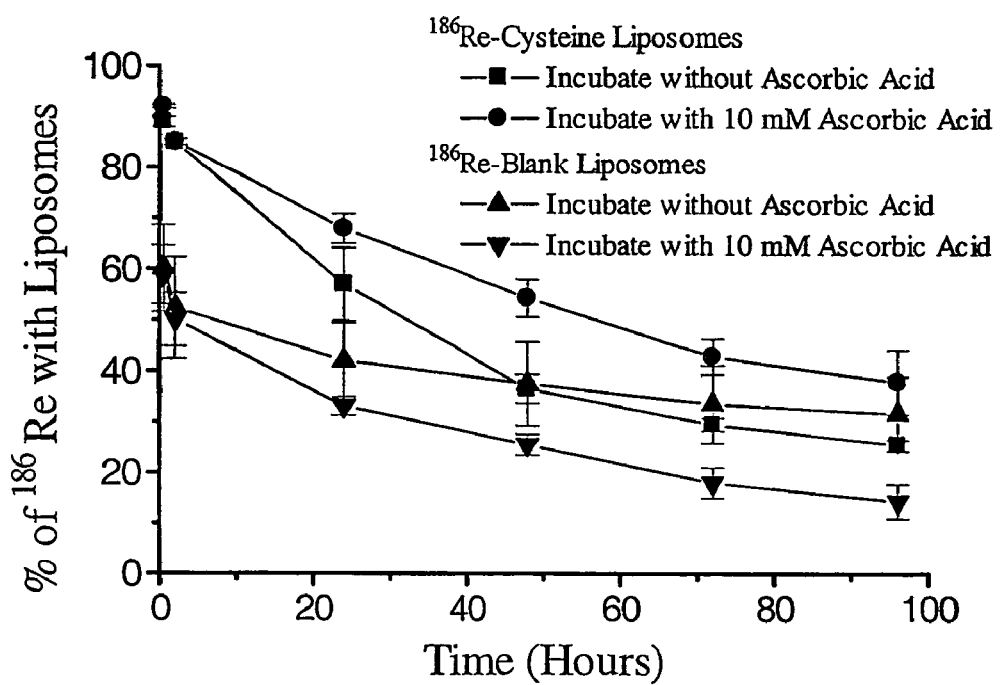

FIG. 7 shows the in vitro stability of $^{186}$Re-liposomes labeled with $^{186}$Re-"BMEDA" (FIG. 7A) or with $^{186}$Re- "BMEDA+BT" (FIG. 7B). It showed that $^{186}$Re-liposomes labeled with $^{186}$Re-"BMEDA" were stable. $^{186}$Re was released gradually and slowly from the liposomes. After incubation for 96 hours at 37° C. with 50% serum-PBS buffer, there was over 40% of radioisotope associated with liposomes. FIG. 7 also shows that there was higher in vitro stability of $^{186}$Re-Cysteine liposomes in the presence of ascorbic acid. Ascorbic acid is an antioxidant, which may protect $^{186}$Re complexes from being oxidized back to perrhenate. $^{186}$Re-Blank liposomes showed lower in vitro stability at earlier time points of incubation.

Effect of Encapsulated GSH on Labeling Efficiency and In Vitro Stability of $^{99m}$Tc-Liposomes The effect of the presence of a thiol compound such as glutathione (GSH) or cysteine encapsulated in the liposomes on labeling efficiency and in vitro stability was determined. Liposomes composed of the same lipid formulation, were prepared in the same manner as GSH liposomes except the liposomes only encapsulated PBS buffer, pH 6.3. Liposomes encapsulating only PBS (Blank liposomes) or GSH-PBS (GSH liposomes) were labeled with either $^{99m}$Tc-"BMEDA" or $^{99m}$Tc-"BMEDA+BT" for 2 hours at 25° C. Labeling efficiencies for the Blank liposomes were 22.3±13.6% (n=3) using $^{99m}$Tc-"BMEDA" and 32.1±17.2% (n=3) using $^{99m}$Tc-"BMEDA+BT". These labeling efficiencies were significantly lower compared with GSH liposomes labeled with either $^{99m}$Tc-"BMEDA" 36.9±10.8% (n=3) or $^{99m}$Tc-"BMEDA+BT" 54.7±12.7% (n=3).

Figure 2A:
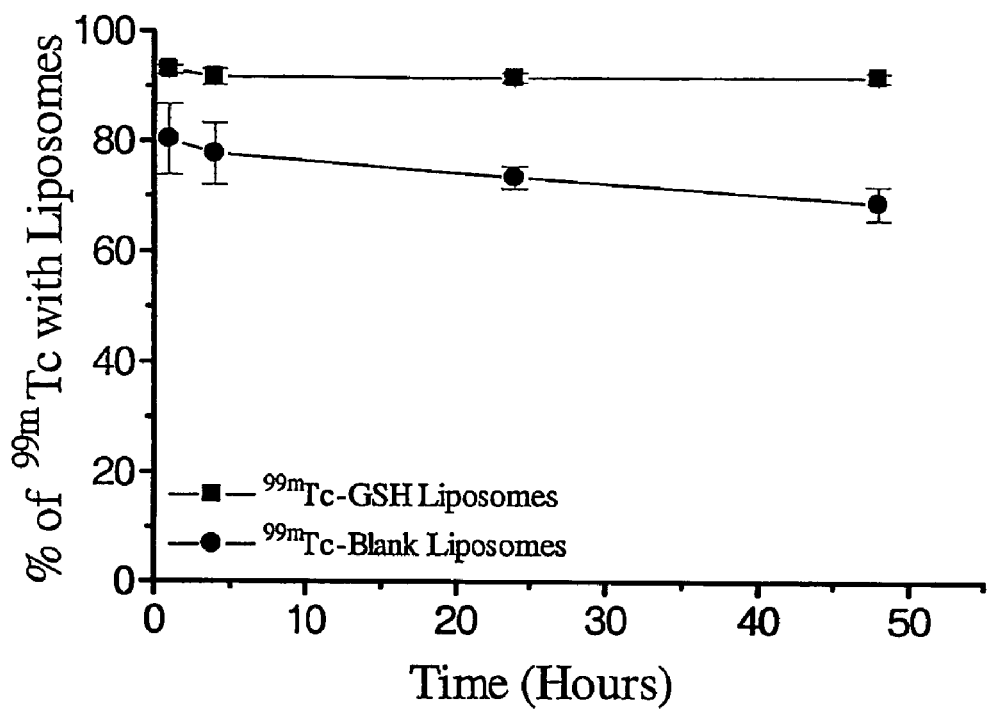
FIG. 2 shows the in vitro stability in PBS buffer (average of three separate experiments) of $^{99m}$Tc-GSH liposomes labeled by using different kinds of $^{99m}$Tc-"SNS/S" complexes at room temperature compared with $^{99m}$Tc-Blank liposomes. Graph A shows the results of $^{99m}$Tc-liposomes labeled with $^{99m}$Tc-"BMEDA". Graph B shows the results of $^{99m}$Tc-liposomes labeled with $^{99m}$Tc-"BMELDA+BT".
Figure 2B:
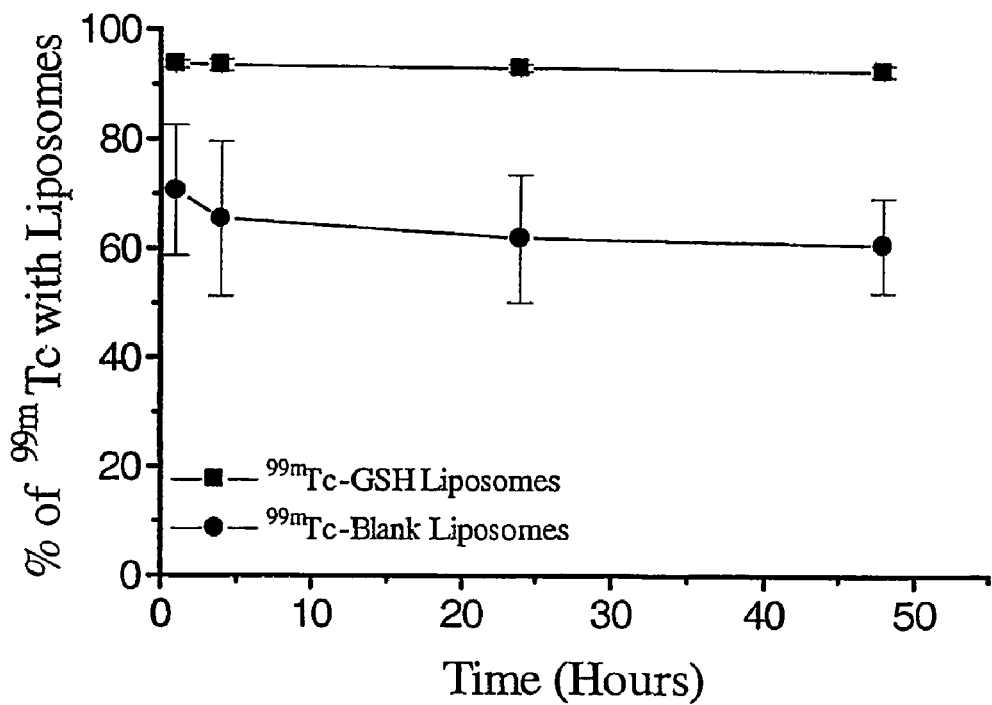

In vitro stability of the $^{99m}$Tc-GSH liposomes and $^{99m}$Tc-Blank liposomes in PBS buffer, pH 6.3, at 25° C. labeled using either $^{99m}$Tc-"BMEDA" or $^{99m}$Tc-"BMEDA+BT" are shown in FIG. 2. For both $^{99m}$Tc-"BMEDA" and $^{99m}$Tc-"BMEDA+BT", the $^{99m}$Tc-GSH liposomes were very stable compared with the $^{99m}$Tc-Blank liposomes, with >90% of the $^{99m}$Tc activity remaining with the liposomes for 48 hours. On the contrary, after 1 hour of incubation, $^{99m}$Tc-Blank liposomes had only 70-80% of the activity associated with the liposomes, and the $^{99m}$Tc activity continued to dissociate from the blank liposomes over the 48 hour incubation period. $^{99m}$Tc-Blank liposomes had significantly lower in vitro stability in PBS buffer compared with $^{99m}$Tc-GSH liposomes.

Figure 3A:
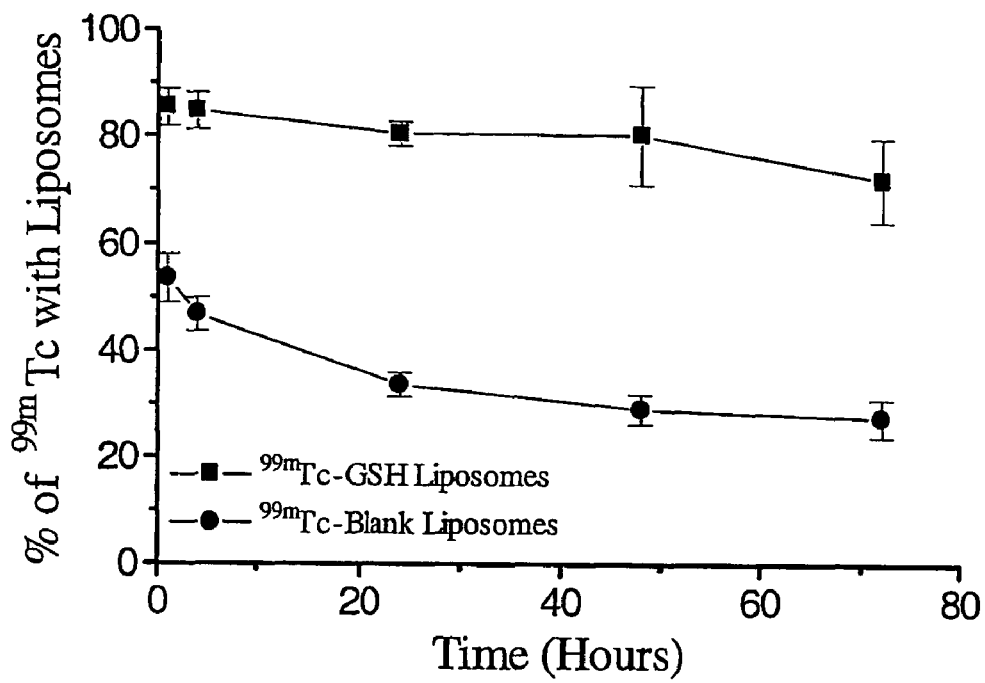
FIG. 3 shows the in vitro stability (average of three separate experiments) of $^{99m}$Tc-GSH liposomes labeled by using different kinds of $^{99m}$Tc-"SNS/S" complexes at 37° C. in 50% serum-PBS buffer compared with $^{99m}$Tc-Blank liposomes. Graph A shows the results of $^{99m}$Tc-liposomes labeled with $^{99m}$Tc-"BMEDA". Graph B shows the results of $^{99m}$Tc-liposomes labeled with $^{99m}$Tc-"BMEDA+BT".
Figure 3B:
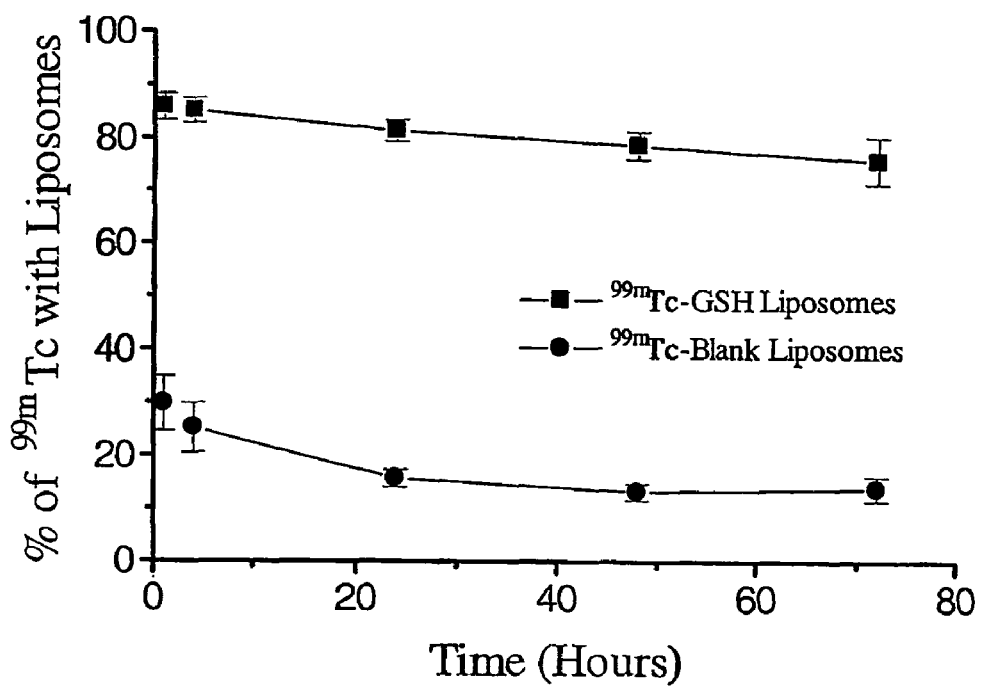

In vitro stability for $^{99m}$Tc-GSH liposomes and $^{99m}$Tc-Blank liposomes after incubation in PBS buffer, pH 7.4, containing 50% serum at 37° C. is shown is FIG. 3. $^{99m}$Tc-GSH liposomes were more stable than $^{99m}$Tc-Blank liposomes after incubation in serum. After 1 hour of incubation, $^{99m}$Tc activity associated with Blank liposomes was only 55% or 30% for $^{99m}$Tc-Blank liposomes labeled with $^{99m}$Tc-"BMEDA" or $^{99m}$Tc-"BMEDA+BT", respectively. These results show the importance of the encapsulated GSH for the in vitro stability of liposomes labeled with either $^{99m}$Tc-"BMEDA" or $^{99m}$Tc-"BMEDA+BT". $^{99m}$Tc-Blank liposomes had significantly lower in vitro stability in 50% serum-PBS buffer compared with $^{99m}$Tc-GSH liposomes.

Normal Rat Biodistribution

Figure 6:
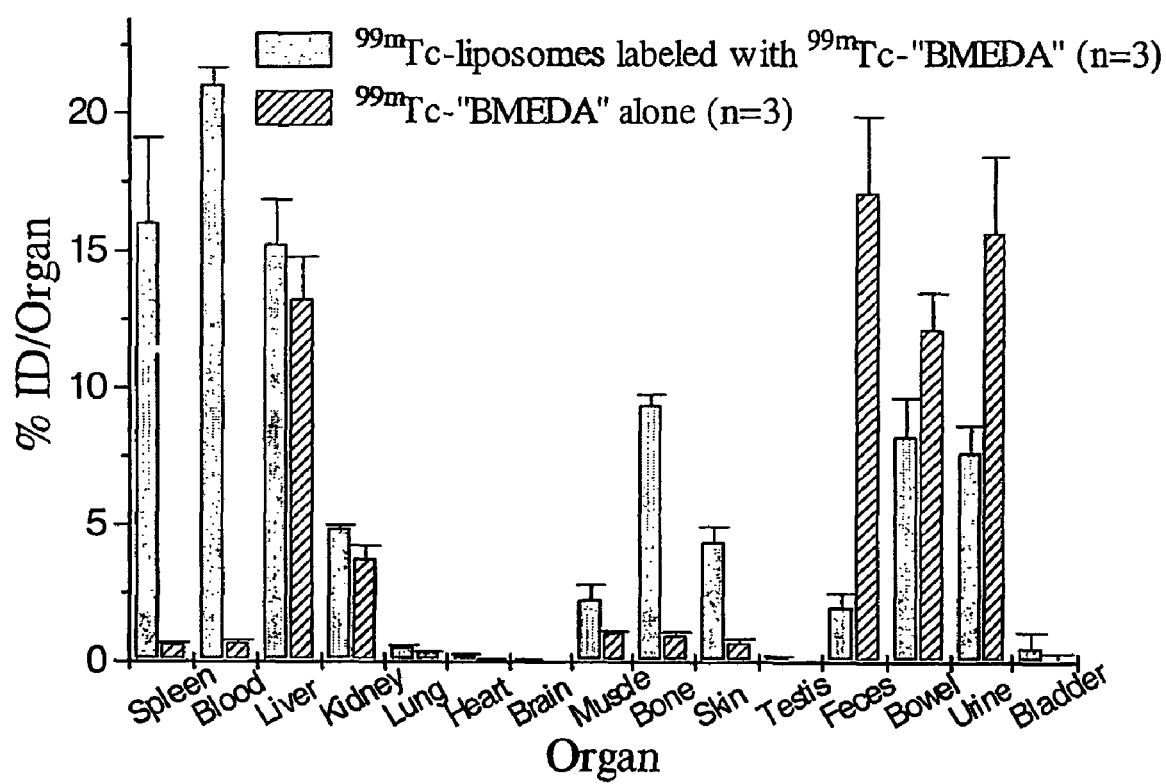
FIG. 6 shows normal rat distribution of $^{99m}$Tc-100 nm GSH liposomes labeled with $^{99m}$Tc-"BMEDA" and $^{99m}$Tc-"BMEDA" alone at 20 hours after intravenous injection. The graph shows the significant difference in behavior of $^{99m}$Tc-100 nm GSH liposomes labeled with $^{99m}$Tc-"BMEDA" compared with $^{99m}$Tc-"BMEDA" alone in rats. $^{99m}$Tc-100 nm GSH liposomes showed the typical liposome distribution behavior with spleen accumulation and slow blood clearance, but $^{99m}$Tc-"BMEDA" alone does not.

Normal rat distributions of $^{99m}$Tc-liposomes labeled with three $^{99m}$Tc-"SNS/S" complexes at 20 hours are listed in Tables 1 and 2. For comparison, biodistributions of the $^{99m}$Tc-"SNS/S" complexes used for liposome labeling were also performed. FIG. 6 shows the biodistributions of $^{99m}$Tc-liposomes labeled with $^{99m}$Tc-"BMEDA" and $^{99m}$Tc-"BMEDA" alone. It can be seen that the in vitro distribution of the $^{99m}$Tc-liposomes labeled with $^{99m}$Tc-"BMEDA" is very different from the free compound alone. $^{99m}$Tc-liposomes were removed from the blood pool slowly and accumulated in the spleen. At 20 hours after intravenous injection of $^{99m}$Tc-liposomes labeled with $^{99m}$Tc-"BMEDA", there was 21.1±0.6% (n=3) of injected dose existing in blood pool, and 16.0±3.1% in spleen. After intravenous injection of $^{99m}$Tc-liposomes labeled with $^{99m}$Tc-"BMEDA+BT", there was 20.4±2.4% (n=4) in blood pool, 14.0±1.2% in spleen. After intravenous injection of $^{99m}$Tc-liposomes labeled with $^{99m}$Tc-"BMBuA," there was 7.5±0.9% (n=3) in blood pool, 5.5±0.5% in spleen. When only $^{99m}$Tc-"SNS/S" complexes were injected, there was much faster excretion from the rat blood pool, and there is no apparent spleen accumulation.

Typical liposome distributions via intravenous injection have the following characteristics: 1) slow blood pool clearance and 2) spleen accumulation. The experiments demonstrated the stability of $^{99m}$Tc-liposomes labeled with $^{99m}$Tc-"BMEDA" and with $^{99m}$Tc-"BMEDA+BT". $^{99m}$Tc-liposomes labeled with $^{99m}$Tc-"BMBuA" showed some spleen accumulation but it was much lower than that of $^{99m}$Tc-liposomes labeled with $^{99m}$Tc-"BMEDA" and with $^{99m}$Tc-"BMEDA+BT." There is an agreement between the biodistribution results and the in vitro stability results, in that the stability of $^{99m}$Tc-liposomes labeled with $^{99m}$Tc-"BMBuA" is lower.

$^{99m}$Tc-100 nm GSH liposomes labeled with $^{99m}$Tc-"BMEDA" and $^{99m}$Tc-"BMEDA+BT" showed significant spleen accumulation at 20 hours after intravenous injection (Tables 1 and 2). In addition, there was still 21.08±0.62% and 20.39±2.40% of injected dose in blood pool for $^{99m}$Tc-100 nm GSH liposomes labeled with $^{99m}$Tc-"BMEDA" and $^{99m}$Tc-"BMEDA+BT". These are common distribution patterns of liposomes after intravenous injection in rats. $^{99m}$Tc-100 nm GSH liposomes labeled with $^{99m}$Tc-"BMBuA" had lower uptake in spleen and blood pool, but higher uptake in the liver. These results show that $^{99m}$Tc-100 nm GSH liposomes labeled with $^{99m}$Tc-"BMBuA" has lower in vivo stability compared with $^{99m}$Tc-100 nm GSH liposomes labeled with $^{99m}$Tc-"BMEDA" or $^{99m}$Tc-"BMEDA+BT".

$^{186}$Re-100 nm cysteine liposomes and $^{186}$Re-Blank liposomes labeled with $^{186}$Re-"BMEDA" showed significant spleen accumulation at 72 hours after intravenous injection (Tables 3 and 4). This shows the common feature of liposome distribution after intravenous injection in rats. $^{186}$Re-100 nm blank liposomes labeled with $^{186}$Re-"BMEDA" showed higher uptake in spleen, but also higher uptake in liver and higher uptake in feces and bowel. $^{186}$Re-"BMEDA" alone did not show the spleen accumulation behavior.

TABLE 1

Normal rat distribution of $^{99m}$Tc-100 nm GSH liposomes (% ID/organ) labeled with different kinds of $^{99m}$Tc-"SNS/S" complexes at 20 hours after intravenous injection.

| | $^{99m}$Tc-Liposomes Labeled with | | |
|---|---|---|---|
| | $^{99m}$Tc-"BMEDA" (N = 3) | $^{99m}$Tc-"BMEDA + BT" (N = 4) | $^{99m}$Tc-"BMBuA" (N = 3) |
| Organ | % ID/Organ (Average ± Sd) | | |
| Spleen | 16.04 ± 3.06 | 13.97 ± 1.20 | 5.46 ± 0.49 |
| Blood | 21.08 ± 0.62 | 20.39 ± 2.40 | 7.76 ± 0.86 |
| Liver | 15.26 ± 1.59 | 13.33 ± 2.22 | 22.66 ± 1.27 |
| Kidney | 4.86 ± 0.13 | 5.01 ± 1.06 | 3.42 ± 0.16 |
| Lung | 0.54 ± 0.05 | 0.43 ± 0.07 | 0.40 ± 0.04 |
| Heart | 0.26 ± 0.02 | 0.14 ± 0.02 | 0.14 ± 0.01 |
| Brain | 0.069 ± 0.007 | 0.062 ± 0.014 | 0.032 ± 0.001 |
| Muscle | 2.29 ± 0.53 | 2.22 ± 1.29 | 1.80 ± 0.46 |
| Bone | 9.40 ± 0.39 | 6.79 ± 1.66 | 3.48 ± 0.13 |
| Skin | 4.39 ± 0.55 | 2.50 ± 0.92 | 2.12 ± 0.28 |
| Testis | 0.20 ± 0.02 | 0.13 ± 0.02 | 0.14 ± 0.01 |
| Feces | 2.00 ± 0.51 | 1.78 ± 1.64 | 14.56 ± 4.82 |

TABLE 1-continued

Normal rat distribution of $^{99m}$Tc-100 nm GSH liposomes (% ID/organ) labeled with different kinds of $^{99m}$Tc-"SNS/S" complexes at 20 hours after intravenous injection.

| | $^{99m}$Tc-Liposomes Labeled with | | |
|---|---|---|---|
| Organ | $^{99m}$Tc-"BMEDA" (N = 3) | $^{99m}$Tc-"BMEDA + BT" (N = 4) | $^{99m}$Tc-"BMBuA" (N = 3) |
| | % ID/Organ (Average ± Sd) | | |
| Bowel | 8.26 ± 1.42 | 7.51 ± 3.18 | 17.97 ± 2.60 |
| Urine | 7.67 ± 0.99 | 11.23 ± 2.35 | 5.15 ± 0.21 |
| Bladder | 0.52 ± 0.56 | 0.57 ± 0.57 | 0.23 ± 0.19 |

TABLE 2

Normal rat distribution of $^{99m}$Tc-100 nm GSH liposomes (% ID/gram) labeled with different kinds of $^{99m}$Tc-"SNS/S" complexes at 20 hours after intravenous injection.

| | $^{99m}$Tc-Liposomes Labeled with | | |
|---|---|---|---|
| Organ | $^{99m}$Tc-"BMEDA" (N = 3) | $^{99m}$Tc-"BMEDA + BT" (N = 4) | $^{99m}$Tc-"BMBuA" (N = 3) |
| | % ID/gram (Average ± Sd) | | |
| Spleen | 25.56 ± 3.98 | 22.26 ± 2.84 | 7.98 ± 0.56 |
| Blood | 1.26 ± 0.06 | 1.11 ± 0.12 | 0.56 ± 0.06 |
| Liver | 1.42 ± 0.04 | 1.19 ± 0.07 | 2.21 ± 0.18 |
| Kidney | 2.38 ± 0.17 | 2.39 ± 0.42 | 1.75 ± 0.10 |
| Lung | 0.41 ± 0.03 | 0.31 ± 0.06 | 0.29 ± 0.04 |
| Heart | 0.25 ± 0.02 | 0.15 ± 0.03 | 0.16 ± 0.01 |
| Brain | 0.042 ± 0.007 | 0.042 ± 0.004 | 0.020 ± 0.001 |
| Muscle | 0.018 ± 0.004 | 0.016 ± 0.008 | 0.018 ± 0.004 |
| Bone | 0.30 ± 0.03 | 0.20 ± 0.05 | 0.14 ± 0.004 |
| Skin | 0.109 ± 0.012 | 0.055 ± 0.015 | 0.064 ± 0.009 |
| Testis | 0.064 ± 0.003 | 0.039 ± 0.004 | 0.042 ± 0.012 |
| Feces | 0.066 ± 0.016 | 0.143 ± 0.129 | 0.486 ± 0.148 |
| Bowel | 0.17 ± 0.03 | 0.19 ± 0.08 | 0.36 ± 0.05 |
| Urine | 0.26 ± 0.01 | 0.37 ± 0.11 | 0.11 ± 0.005 |
| Bladder | 0.84 ± 0.53 | 0.76 ± 0.50 | 0.44 ± 0.23 |

TABLE 3

Normal rat distribution of $^{186}$Re-100 nm Cysteine liposomes labeled with $^{186}$Re-"BMEDA", $^{186}$Re-100 nm Blank liposomes labeled with $^{186}$Re-"BMEDA" and $^{186}$Re-"BMEDA" alone (% ID/organ) at 72 hours after intravenous injection.

| | Agents | | |
|---|---|---|---|
| Organ | $^{186}$Re-Cysteine Liposomes Labeled with $^{186}$Re-"BMEDA" (N = 4) | $^{186}$Re-Blank Liposomes Labeled with $^{186}$Re-"BMEDA" (N = 4) | $^{186}$Re-"BMEDA" Alone (N = 4) |
| | % ID/Organ (Average ± Sd) | | |
| Spleen | 3.88 ± 0.44 | 7.90 ± 0.57 | 0.21 ± 0.05 |
| Blood | 0.32 ± 0.05 | 0.78 ± 0.19 | 0.49 ± 0.04 |
| Liver | 8.55 ± 0.61 | 19.56 ± 1.15 | 5.97 ± 0.35 |
| Kidney | 5.22 ± 0.48 | 4.23 ± 0.47 | 10.42 ± 0.93 |
| Lung | 0.12 ± 0.02 | 0.13 ± 0.02 | 0.37 ± 0.06 |
| Heart | 0.027 ± 0.004 | 0.031 ± 0.004 | 0.076 ± 0.005 |
| Brain | 0.0026 ± 0.0006 | 0.0039 ± 0.0007 | 0.0052 ± 0.0007 |
| Muscle | 0.57 ± 0.14 | 0.81 ± 0.10 | 0.79 ± 0.07 |
| Femur | 1.28 ± 0.20 | 3.44 ± 0.77 | 0.58 ± 0.06 |
| Skin | 0.84 ± 0.22 | 1.34 ± 0.80 | 1.48 ± 0.51 |
| Testis | 0.044 ± 0.014 | 0.051 ± 0.008 | 0.058 ± 0.004 |
| Feces | 6.08 ± 0.57 | 13.71 ± 3.51 | 20.54 ± 4.35 |
| Bowel | 5.38 ± 1.44 | 5.95 ± 2.00 | 6.67 ± 3.31 |
| Urine | 50.09 ± 15.30 | 29.09 ± 6.83 | 26.93 ± 4.23 |

TABLE 4

Normal rat distribution of $^{186}$Re-100 nm Cysteine liposomes labeled with $^{186}$Re-"BMEDA", $^{186}$Re-100 nm Blank liposomes labeled with $^{186}$Re-"BMEDA" and $^{186}$Re-"BMEDA" alone (% ID/gram) at 72 hours after intravenous injection.

| | Agents | | |
|---|---|---|---|
| Organ | $^{186}$Re-Cysteine Liposomes Labeled with $^{186}$Re-"BMEDA" (N = 4) | $^{186}$Re-Blank Liposomes Labeled with $^{186}$Re-"BMEDA" (N = 4) | $^{186}$Re-"BMEDA" Alone (N = 4) |
| | % ID/Gram (Average ± Sd) | | |
| Spleen | 12.03 ± 1.51 | 25.93 ± 4.88 | 0.38 ± 0.14 |
| Blood | 0.013 ± 0.001 | 0.035 ± 0.010 | 0.022 ± 0.001 |
| Liver | 0.71 ± 0.08 | 1.90 ± 0.32 | 0.54 ± 0.05 |
| Kidney | 2.02 ± 0.26 | 1.84 ± 0.32 | 4.49 ± 0.37 |
| Lung | 0.060 ± 0.021 | 0.081 ± 0.027 | 0.23 ± 0.03 |
| Heart | 0.022 ± 0.004 | 0.026 ± 0.004 | 0.069 ± 0.007 |
| Brain | 0.0016 ± 0.0003 | 0.0023 ± 0.0007 | 0.0035 ± 0.0007 |
| Muscle | 0.0032 ± 0.0009 | 0.0048 ± 0.0008 | 0.0048 ± 0.0005 |
| Femur | 0.028 ± 0.004 | 0.082 ± 0.020 | 0.014 ± 0.000 |
| Skin | 0.014 ± 0.004 | 0.025 ± 0.015 | 0.029 ± 0.012 |
| Testis | 0.012 ± 0.005 | 0.014 ± 0.002 | 0.015 ± 0.003 |
| Feces | 1.83 ± 0.65 | 3.35 ± 1.49 | 4.82 ± 1.53 |
| Bowel | 0.24 ± 0.05 | 0.31 ± 0.12 | 0.34 ± 0.19 |
| Urine | 1.06 ± 0.47 | 0.76 ± 0.25 | 0.79 ± 0.08 |

Figure 4:
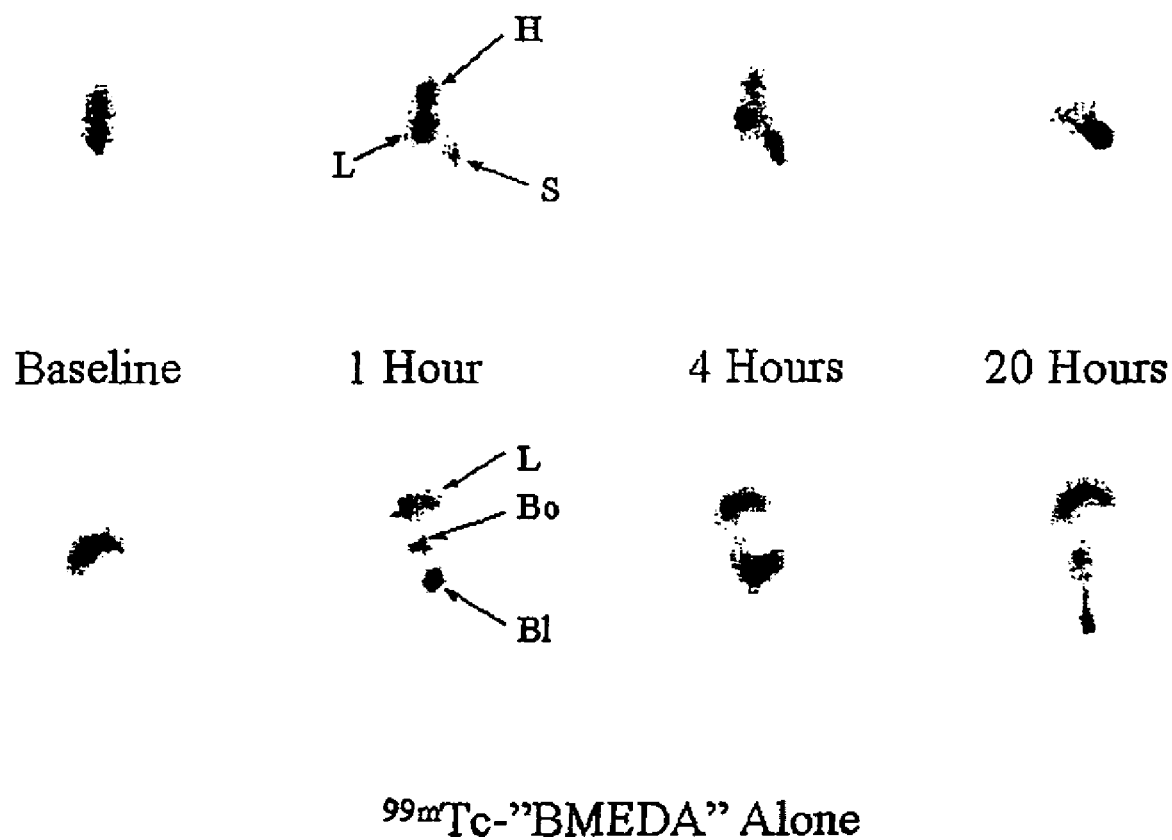
FIG. 4 shows gamma camera images of normal rats via intravenous injection method. The upper panel shows the images of a rat at baseline, 1 hour, 4 hours and 20 hours after intravenous injection of $^{99m}$Tc-100 nm GSH liposomes labeled with $^{99m}$Tc-"BMEDA". For comparison, the lower panel shows the images of a rat at the corresponding times after intravenous injection of $^{99m}$Tc-"BMEDA" alone. $^{99m}$Tc-100 nm GSH liposomes labeled with $^{99m}$Tc-"BMEDA" showed significant spleen accumulation and slow blood clearance, which are the common features of liposome distribution after intravenous injection in rats. $^{99m}$Tc-"BMEDA" alone showed fast blood clearance, fast excretion into bowel and urine, and no spleen accumulation. (H: Heart; S: Spleen; L: Liver; Bo: Bowel; Bl: Bladder.)
Figure 5:
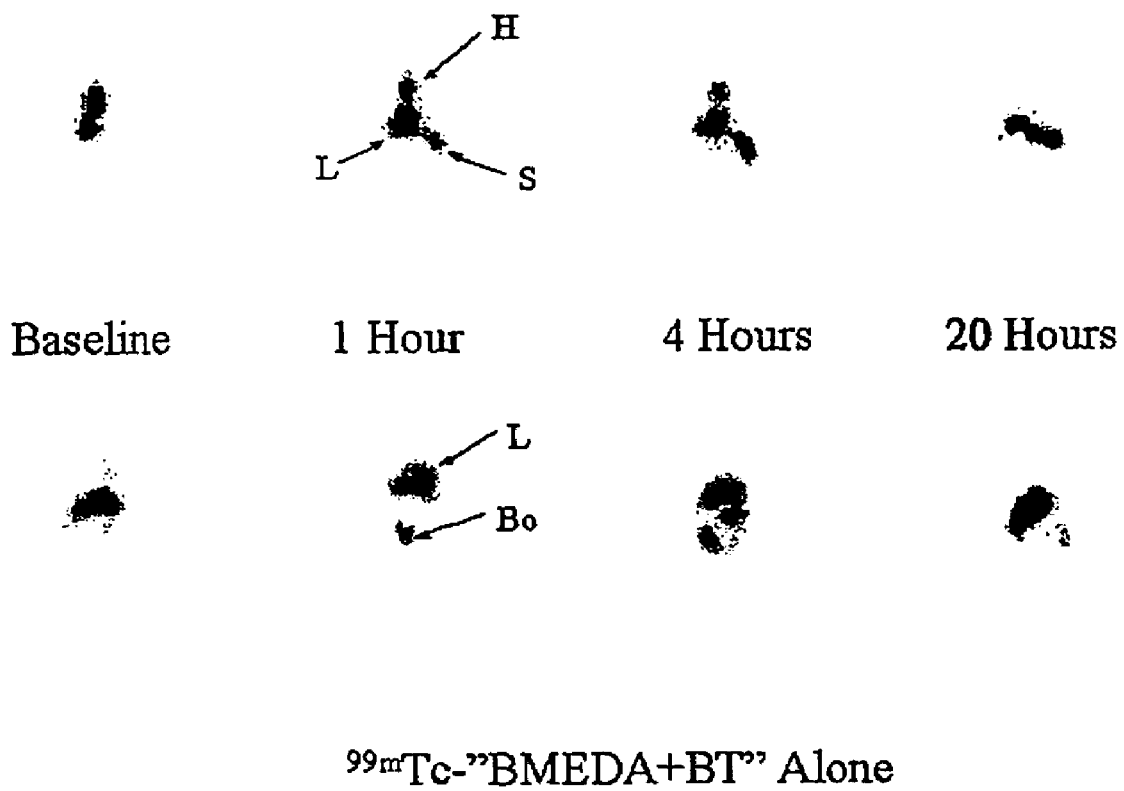
FIG. 5 shows gamma camera images of normal rats via intravenous injection method. The upper panel shows the images of a rat at baseline, 1 hour, 4 hours and 20 hours after intravenous injection of $^{99m}$Tc-100 nm GSH liposomes labeled with $^{99m}$Tc-"BMEDA+BT". For comparison, the lower panel shows the images of a rat at the corresponding times after intravenous injection of $^{99m}$Tc-"BMEDA+BT" alone. $^{99m}$Tc-100 nm GSH liposomes labeled with $^{99m}$Tc-"BMEDA+BT" showed significant spleen accumulation and slow blood clearance, which are the common features of liposome distribution after intravenous injection in rats. $^{99m}$Tc-"BMEDA" alone showed fast blood clearance, fast excretion into bowel and urine, and no spleen accumulation. (H: Heart; S: Spleen; L: Liver; Bo: Bowel.)

FIG. 4 shows the gamma camera images of two rats at different times after intravenous injection of $^{99m}$Tc-liposomes labeled with $^{99m}$Tc-"BMEDA" and $^{99m}$Tc-"BBMEDA" alone, respectively. From the images, significant differences between $^{99m}$Tc-liposome labeled with $^{99m}$Tc-"BMEDA" and $^{99m}$Tc-"BMEDA" alone were observed. FIG. 5 shows the gamma camera images of two rats at different times after intravenous injection of $^{99m}$Tc-liposomes labeled with $^{99m}$Tc-"BMEDA+BT" and $^{99m}$Tc-"BMEDA+BT" alone, respectively. From the images, significant differences between $^{99m}$Tc-liposome labeled with $^{99m}$Tc-"BMEDA+BT" and $^{99m}$Tc-"BMEDA+BT" alone were observed.

Figure 9:
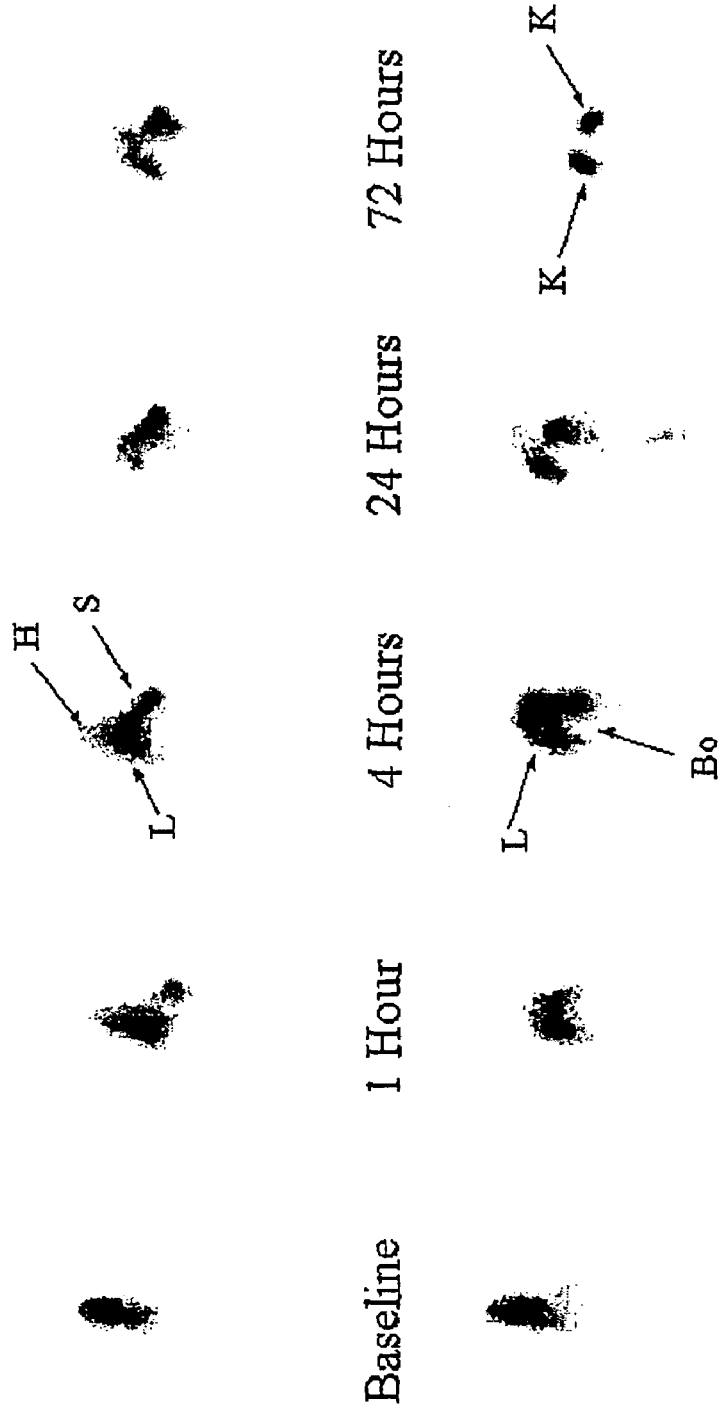
FIG. 9 shows gamma camera images of normal rats with the intravenous injection method. The upper panel shows the images of a rat at baseline, 1 hour, 4 hours, 24 hours, and 72 hours after intravenous injection of $^{186}$Re-100 nm Cysteine liposomes labeled with $^{186}$Re-"BMEDA". For comparison, the lower panel shows the images of a rat at the corresponding times after intravenous injection of $^{186}$Re-"BMEDA" alone. $^{186}$Re-100 nm Cysteine liposomes labeled with $^{186}$Re-"BMEDA" showed significant spleen accumulation and slow blood clearance, which are the common features of liposome distribution after intravenous injection in rats. $^{186}$Re-"BMEDA" alone showed fast blood clearance, fast excretion into bowel and urine, and no spleen accumulation. (H: Heart; S: Spleen; L: Liver; Bo: Bowel; K: Kidney.)

FIG. 9 shows the gamma camera images of a rat acquired at different times after intravenous injection of $^{186}$Re-Cysteine liposomes labeled with $^{186}$Re-"BMEDA." It showed spleen accumulation behavior and this accumulation is stable even at 72 hours after intravenous injection. FIG. 9 also compares the biodistribution of rats injected with $^{186}$Re-liposomes labeled with $^{186}$Re-"BMEDA" or $^{186}$Re-"BMEDA" alone. $^{186}$Re-"BMEDA" alone showed significant excretion from the hepatobiliary system and no apparent spleen accumulation. $^{186}$Re-liposomes showed spleen accumulation and much lower excretion from the hepatobiliary system. Biodistribufion at 72 hours after intravenous injection showed that a higher level of rhenium was excreted via urinary tract for $^{186}$Re-liposomes.

Labeling Ratio of $^{99m}$Tc-Liposomes and $^{186}$Re-Liposomes

The average labeling ratio of $^{99m}$Tc-liposomes from three separate experiments is from 36.9-69.2% (Table 5) at 2 hours after room temperature incubation with liposomes. The labeling ratio of $^{186}$Re-liposomes is similar with that of $^{99m}$Tc-liposomes with same labeling condition. Table 6 provides the labeling ratio of several $^{186}$Re-liposomes of the invention labeled at 37° C. for 1 hour.

TABLE 5

The labeling ratio (average of three separate experiments) of $^{99m}$Tc-GSH liposomes labeled with different $^{99m}$Tc-"SNS/S" complexes.

| $^{99m}$Tc-Liposome from | $^{99m}$Tc-"BMEDA" | $^{99m}$Tc-"BMEDA + BT" | $^{99m}$Tc-"BMBuA" | $^{99m}$Tc-"BMBuA + BT" |
|---|---|---|---|---|
| Labeling Ratio at 2 hours (mean ± sd) (%) | 36.9 ± 10.8 | 54.7 ± 12.7 | 69.2 ± 10.2 | 54.8 ± 0.8 |

TABLE 6

The labeling ratio (average of six separate experiments) of $^{186}$Re-liposomes labeled with $^{186}$Re-"SNS/S" complexes at 37° C. for 1 hour.

| | Liposome Type | | | |
|---|---|---|---|---|
| | Cysteine Liposomes | | Blank Liposomes | |
| $^{186}$Re-Liposomes from | $^{186}$Re-"BMEDA" | $^{186}$Re-"BMEDA + BT" | $^{186}$Re-"BMEDA" | $^{186}$Re-"BMEDA + BT" |
| Labeling Ratio (mean ± sd) (%) | 72.5 ± 5.5 | 77.6 ± 13.0 | 61.6 ± 13.8 | 69.2 ± 5.6 |

Figure 8:
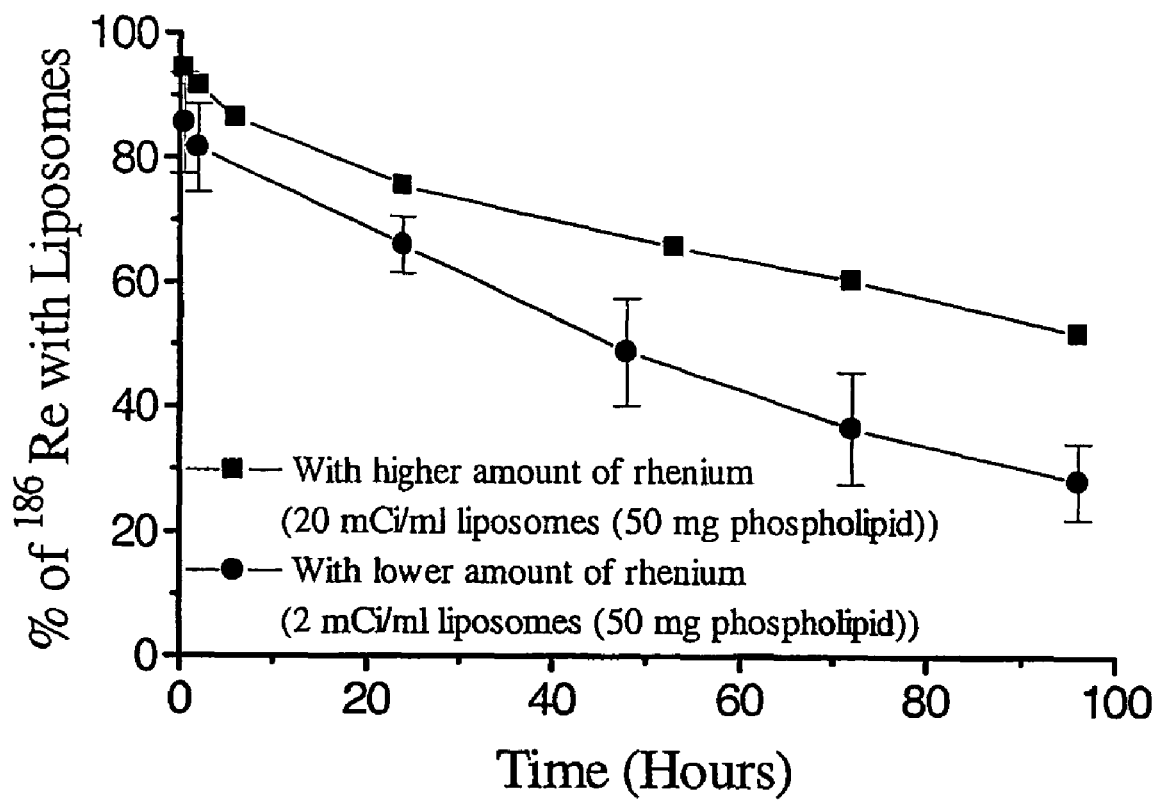
FIG. 8 shows the comparison of in vitro stability of $^{186}$Re-Cysteine liposomes labeled with $^{186}$Re-"BMEDA" having two different specific activities with same amount of liposomes.

FIG. 8 also shows that higher in vitro stability was achieved with a higher amount of rhenium, which means that rhenium with a high specific activity can be used to label liposomes using this labeling method. Surprisingly, stability did not decrease as would be expected for higher activity but it was actually increased in the therapeutic range.

Preparation of Liposomes Containing Ammonium Sulfate

Liposomes exhibiting transmembrane pH gradients were prepared from a modification of the method by Maurer-Spurej E et al. in "Factors influencing uptake and retention of amino-containing drugs in large unilamellar vesicles exhibiting transmembrane pH gradients" *Biochimica et Biophysica Acta* 1416: 1-10, 1999. Liposomes were comprised of distearoyl phosphatidylcholine (DSPC) (Avanti Polar Lipids, Pelham, Ala.); cholesterol (Chol) (Calbiochem, San Diego, Calif.); and alpha-tocopherol (Aldrich, Milwaukee, Wis.). All lipids were used without further purification. The lipids were mixed in chloroform at a total molar ratio of 54:44:2 (DSPC:Chol:α-tocopherol). Chloroform was then removed by rotary evaporation to form a lipid film. The lipid film was stored overnight in a vacuum desiccator to remove organic solvent. Samples were rehydrated with 300 mM ammonium sulfate (Sigma, St Louis, Mo.) in sterile water for injection and warmed to 55° C. for 15 minutes with periodic vortexing until all of the lipids were in suspension. The resultant multilamellar vesicles formed from rehydration were then frozen in liquid nitrogen and thawed in 55° C. water bath for 5 times. For some preparations, the suspension was allowed to cool to room temperature and then stored overnight in the refrigerator.

The solutions were then diluted at a volume/volume ratio of 1 part lipid suspension to 1 part 300 mM ammonium sulfate solution. The diluted lipid suspensions were then extruded through a series (2 passes, 2µ; 2 passes, 400 nm; 2 passes, 200 nm; 5 passes, 100 nm) of polycarbonate filters (Lipex Extruder, Vancouver, Canada) at 55° C. The extruded lipid solution was then stored in the refrigerator at 4° C. Immediately before radiolabeling, liposomes were diluted at a volume/volume ratio with 1 part liposomes to 2 parts PBS buffer, pH 7.4, and centrifuged at 47,000×g for 45 minutes. Then, the supernatant was discarded and PBS buffer, pH 7.4, was added to resuspend liposomes. The liposomes were then used for radiolabeling studies.

$^{186}$Re—(NH$_4$)$_2$SO$_4$ Liposome Labeling Protocol

The pH of the $^{186}$Re-"BMEDA" solution prepared above was adjusted to 7.0. Immediately before radiolabeling, the liposomes containing ammonium sulfate were diluted at a volume/volume ratio with 1 part liposomes to 2 parts PBS buffer. pH 7.4, and centrifuged at 47,000×g for 45 minutes to remove the extraliposomal ammonium sulfate. The supernatant was discarded and PBS buffer, pH 7.4, was added to resuspend liposomes. Then, the resultant liposomes were mixed with 0.7 ml of the $^{186}$Re-"BMEDA" solution, and incubated at 25° C. for 2 hours. It is possible to achieve good labeling efficiencies after incubation at 37° C. for 1 hour. The labeling efficiency was determined from the $^{186}$Re-activity associated with the $^{186}$Re-liposomes before and after Sephadex G-25 column separation.

$^{186}$Re—(NH$_4$)$_2$SO$_4$ Liposome Labeling Ratios

The labeling ratio of $^{186}$Re—(NH$_4$)$_2$SO$_4$ liposomes labeled with different $^{186}$Re-"SNS/S" complexes is shown in Table 7.

TABLE 7

The labeling ratio (average of six separate experiments) of $^{186}$Re-liposomes labeled with $^{186}$Re-"SNS/S" complexes at 37° C. for 1 hour.

| | Liposome Type | | | |
|---|---|---|---|---|
| | (NH$_4$)$_2$SO$_4$ Liposomes | | Blank Liposomes | |
| $^{186}$Re-Liposomes Labeled with | $^{186}$Re-"BMEDA" | $^{186}$Re-"BMEDA + BT" | $^{186}$Re-"BMEDA" | $^{186}$Re-"BMEDA + BT" |
| Labeling Ratio (mean ± sd) (%) | 84.6 ± 4.5 | 87.5 ± 2.3 | 61.6 ± 13.8 | 69.2 ± 5.6 |

Figure 10A:
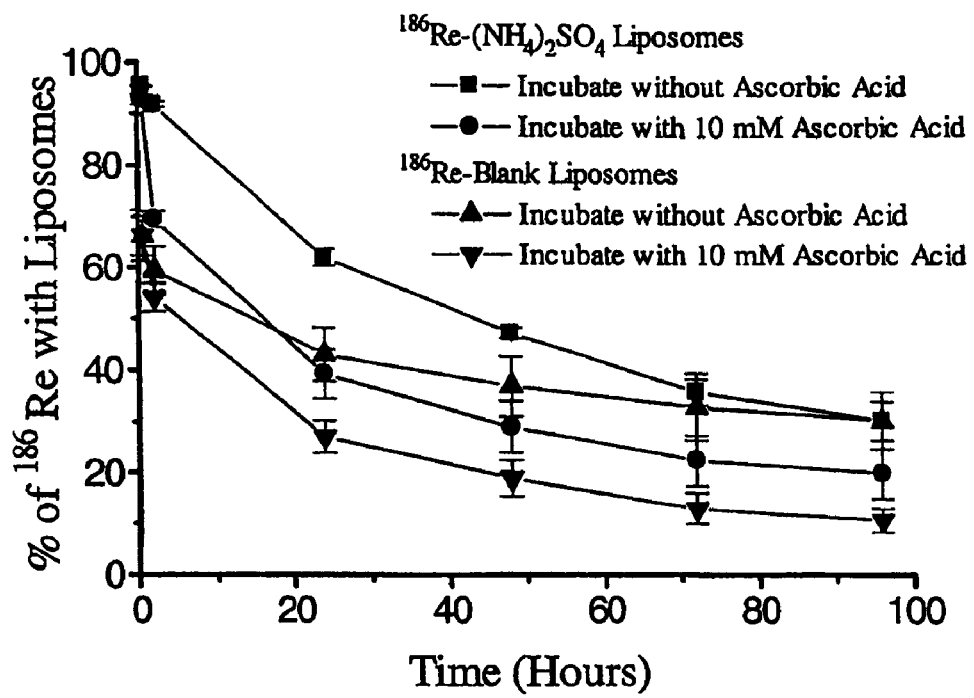
FIG. 10 shows the in vitro stability (average of three separate experiments) of $^{186}$Re—$(NH_4)_2SO_4$ liposomes and $^{186}$Re-Blank liposomes labeled with $^{186}$Re-"BMEDA" (Graph A) or with $^{186}$Re-"BMEDA+BT" (Graph B) in the presence or absence of 10 mM ascorbic acid in 50% serum-PBS buffer at 37° C.
Figure 10B:
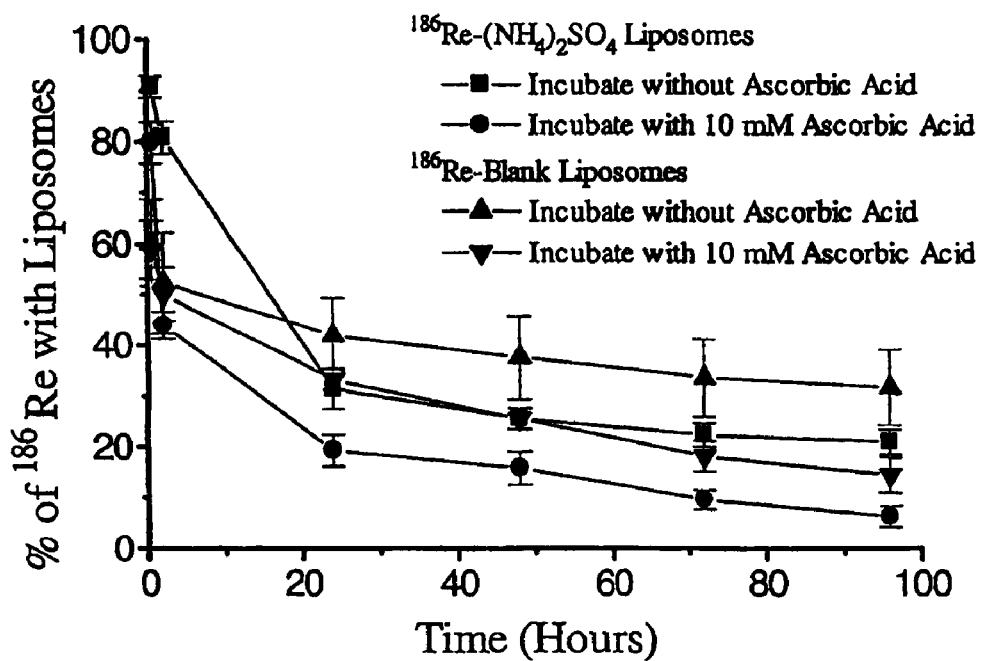
Figure 11:
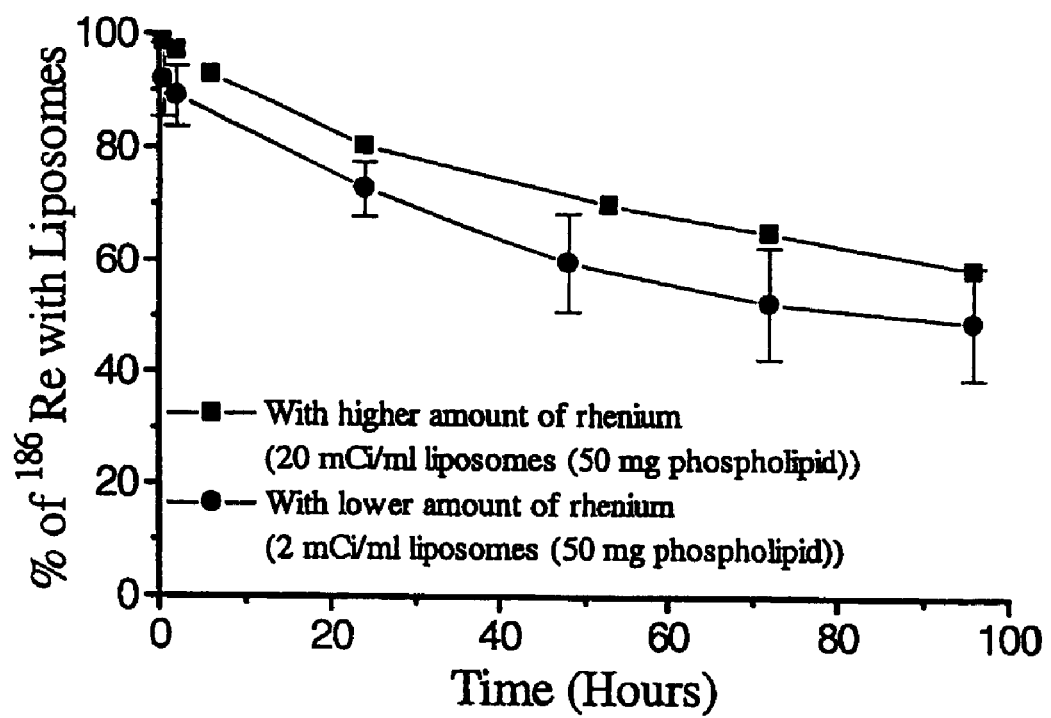
FIG. 11 shows the comparison of in vitro stability of $^{186}$Re—$(NH_4)_2SO_4$ liposomes labeled with $^{186}$Re-"BMEDA" having two different specific activities with same amount of liposomes.

FIG. 10 shows that for $^{186}$Re-liposomes labeled with $^{186}$Re-"BMEDA," $^{186}$Re—(NH$_4$)$_2$SO$_4$ liposomes had higher in vitro stability compared with $^{186}$Re-Blank liposomes. In vitro stability of $^{186}$Re—(NH$_4$)$_2$SO$_4$ liposomes was higher when labeled with $^{186}$Re-"BMEDA" compared with 186Re-"BMEDA+BT." Ascorbic acid did not increase the in vitro stability. FIG. 11 also shows that higher in vitro stability was achieved with a higher amount of rhenium, which means that rhenium with a high specific activity can be used to label liposomes with this labeling method.

Normal Rat Biodistribution

Figure 12:
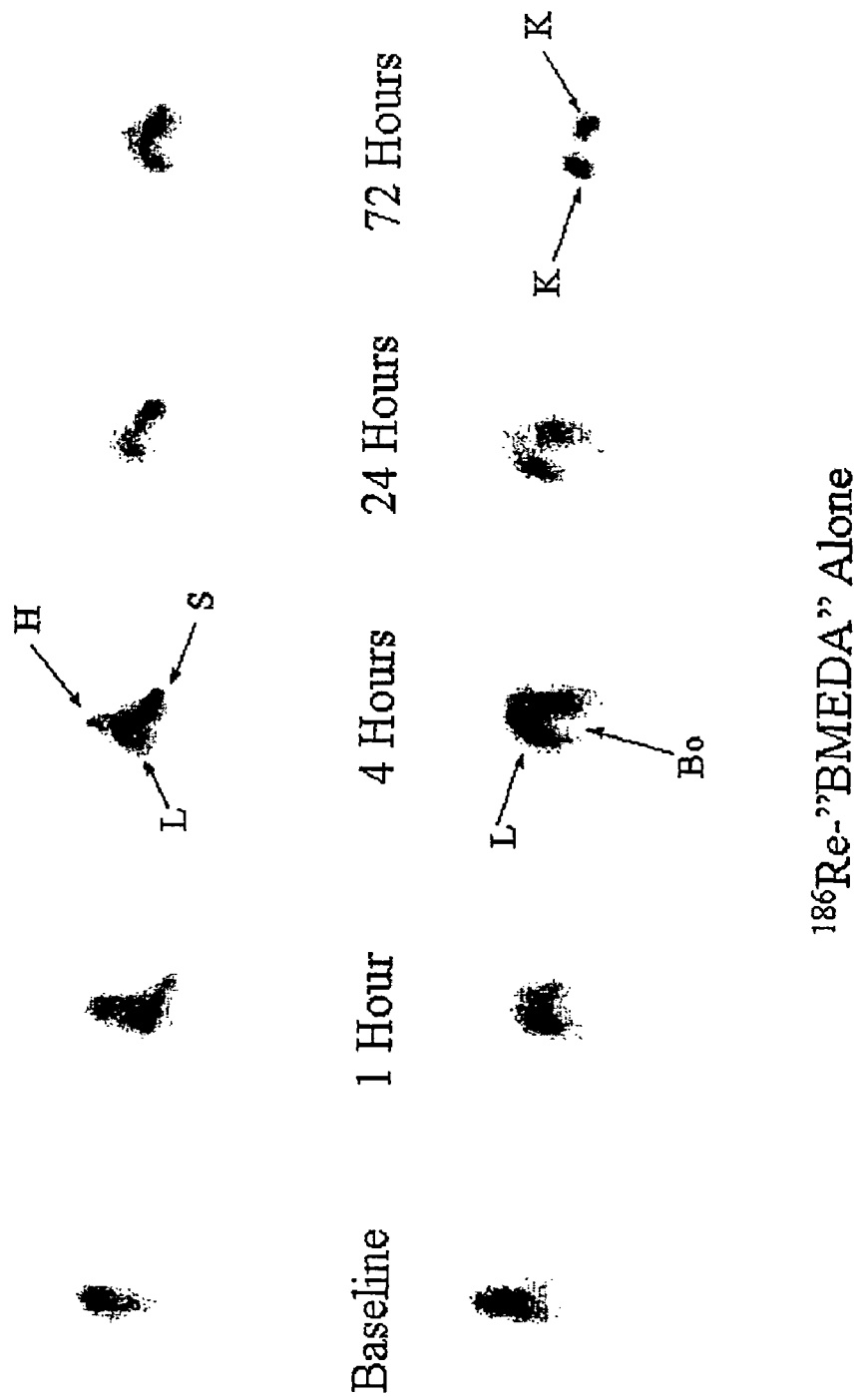
FIG. 12 shows gamma camera images of normal rats via intravenous injection method. The upper panel shows the images of a rat at baseline, 1 hour, 4 hours, 24 hours, and 72 hours after intravenous injection of $^{186}$Re-100 nm $(NH_4)_2SO_4$ liposomes labeled with $^{186}$Re-"BMEDA". For comparison, the lower panel shows the images of a rat at the corresponding times after intravenous injection of $^{186}$Re-"BMEDA" alone. $^{186}$Re-100 nm $(NH_4)_2SO_4$ liposomes labeled with $^{186}$Re-"BMMA" showed significant spleen accumulation and slow blood clearance, which are the common features of liposome distribution after intravenous injection in rats. $^{186}$Re-"BMBDA" alone showed fast blood clearance, fast excretion into bowel and urine, and no spleen accumulation. (H: Heart; S: Spleen; L: Liver; Bo: Bowel; K: Kidney.)

FIG. 12 shows the gamma camera images of two rats at different times after intravenous injection of $^{186}$Re-liposomes labeled with $^{186}$Re-"BMEDA" and $^{186}$Re-"BMDA" alone, respectively. From the images, significant differences between $^{186}$Re-liposome labeled with $^{186}$Re-"BMEDA" and $^{186}$Re-"BMEDA" alone were observed.

Normal rat distributions of $^{186}$Re-liposomes labeled with three $^{186}$Re-"SNS/S" complexes are listed in Tables 8 and 9. $^{186}$Re-100 nm (NH$_4$)$_2$SO$_4$ liposomes and $^{186}$Re-Blank liposomes labeled with $^{186}$Re-"BMEDA" showed significant spleen accumulation at 72 hours after intravenous injection. This shows the common feature of liposome distribution after intravenous injection in rats. $^{186}$Re-100 nm (NH$_4$)$_2$SO$_4$ liposomes labeled with $^{186}$Re-"BMEDA" showed higher ratio in spleen. $^{186}$Re-"BMEDA" alone did not show the spleen accumulation behavior.

TABLE 8

Normal rat distribution of $^{186}$Re-100 nm $(NH_4)_2SO_4$ liposomes labeled with $^{186}$Re-"BMEDA," $^{186}$Re-100 nm Blank liposomes labeled with $^{186}$Re-"BMEDA" and $^{186}$Re-"BMEDA" alone (% ID/organ) at 72 hours after intravenous injection.

| | Agents | | |
|---|---|---|---|
| Organ | $^{186}$Re-$(NH_4)_2SO_4$ Liposomes Labeled with $^{186}$Re-"BMEDA" (N = 4) | $^{186}$Re-Blank Liposomes Labeled with $^{186}$Re-"BMEDA" (N = 4) | $^{186}$Re-"BMEDA" Alone (N = 4) |
| | % ID/Organ (Average ± Sd) | | |
| Spleen | 9.80 ± 0.93 | 7.90 ± 0.57 | 0.21 ± 0.05 |
| Blood | 0.52 ± 0.11 | 0.78 ± 0.19 | 0.49 ± 0.04 |
| Liver | 22.75 ± 0.43 | 19.56 ± 1.15 | 5.97 ± 0.35 |
| Kidney | 8.83 ± 0.09 | 4.23 ± 0.47 | 10.42 ± 0.93 |
| Lung | 0.16 ± 0.02 | 0.13 ± 0.02 | 0.37 ± 0.06 |
| Heart | 0.035 ± 0.002 | 0.031 ± 0.004 | 0.076 ± 0.005 |
| Brain | 0.0037 ± 0.0008 | 0.0039 ± 0.0007 | 0.0052 ± 0.0007 |
| Muscle | 1.01 ± 0.30 | 0.81 ± 0.10 | 0.79 ± 0.07 |
| Femur | 6.14 ± 1.00 | 3.44 ± 0.77 | 0.58 ± 0.06 |
| Skin | 1.44 ± 0.28 | 1.34 ± 0.80 | 1.48 ± 0.51 |
| Testis | 0.082 ± 0.011 | 0.051 ± 0.008 | 0.058 ± 0.004 |
| Feces | 16.26 ± 6.36 | 13.71 ± 3.51 | 20.54 ± 4.35 |
| Bowel | 12.37 ± 3.58 | 5.95 ± 2.00 | 6.67 ± 3.31 |
| Urine | 11.33 ± 0.50 | 29.09 ± 6.83 | 26.93 ± 4.23 |

TABLE 9

Normal rat distribution of $^{186}$Re-100 nm $(NH_4)_2SO_4$ liposomes labeled with $^{186}$Re-"BMEDA," $^{186}$Re-100 nm Blank liposomes labeled with $^{186}$Re-"BMEDA" and $^{186}$Re-"BMEDA" alone (% ID/gram) at 72 hours after intravenous injection.

| | Agents | | |
|---|---|---|---|
| Organ | $^{186}$Re-$(NH_4)_2SO_4$ Liposomes Labeled with $^{186}$Re-"BMEDA" (N = 4) | $^{186}$Re- Blank Liposomes Labeled with $^{186}$Re-"BMEDA" (N = 4) | $^{186}$Re-"BMEDA" Alone (N = 4) |
| | % ID/Gram (Average ± Sd) | | |
| Spleen | 32.50 ± 6.17 | 25.93 ± 4.88 | 0.38 ± 0.14 |
| Blood | 0.020 ± 0.004 | 0.035 ± 0.010 | 0.022 ± 0.001 |
| Liver | 1.82 ± 0.26 | 1.90 ± 0.32 | 0.54 ± 0.05 |
| Kidney | 3.43 ± 0.44 | 1.84 ± 0.32 | 4.49 ± 0.37 |
| Lung | 0.087 ± 0.018 | 0.081 ± 0.027 | 0.23 ± 0.03 |
| Heart | 0.028 ± 0.004 | 0.026 ± 0.004 | 0.069 ± 0.007 |
| Brain | 0.0024 ± 0.0003 | 0.0023 ± 0.0007 | 0.0035 ± 0.0007 |
| Muscle | 0.0054 ± 0.0019 | 0.0048 ± 0.0008 | 0.0048 ± 0.0005 |
| Femur | 0.13 ± 0.03 | 0.082 ± 0.020 | 0.014 ± 0.000 |
| Skin | 0.023 ± 0.005 | 0.025 ± 0.015 | 0.029 ± 0.012 |
| Testis | 0.022 ± 0.004 | 0.014 ± 0.002 | 0.015 ± 0.003 |
| Feces | 3.63 ± 0.49 | 3.35 ± 1.49 | 4.82 ± 1.53 |
| Bowel | 0.52 ± 0.14 | 0.31 ± 0.12 | 0.34 ± 0.19 |
| Urine | 0.39 ± 0.09 | 0.76 ± 0.25 | 0.79 ± 0.08 |

Synthesis of $^{99m}$Tc-"SXS/S"

"BMEDA" was synthesized using a modification of a procedure described by Corbin et al. in "Preparation and properties of tripodal and linear tetradentate N,S-donor ligands and their complexes containing the $MoO_2^{2+}$ core" *Inorganica Chimica Acta.* 1984; 90:41-51. 2-Mercaptoethyl sulfide (MES), 2-mercaptoethyl ether (MEE), benzenthiol (BT) and 2-(dimethylamino) ethanethiol (DMAT) were purchased from Aldrich (Milwaukee, Wis.). First, $^{99m}$Tc-glucoheptonate was prepared by pipetting 1.0 ml of 10 mg/ml glucoheptonate into a vial containing 0.16 mg/ml degassed $SnCl_2$ solution. After mixing, 15 mCi (555 MBq) of $^{99m}$Tc-sodium pertechnetate (Amersham Medi-Physics, San Antonio, Tex.) in 1.0 ml of saline was added. The mixture was stirred at 25° C. for 20 minutes. The labeling efficiency of the $^{99m}$Tc-glucoheptonate was checked by instant thin layer chromatography (ITLC) eluted in methanol, paper chromatography eluted in methanol and paper chromatography eluted in saline.

The following solutions were prepared as follows: BMEDA solution: BMEDA (3.9 mg) (3.5 µl) to a new vial. MRS solution: MES (2.6 mg) (2.2 µl) to a new vial. MEE solution: MEE (2.3 mg) (2.1 µl) to a new vial. BT solution: BT (2.2 mg) (2.0 µl) to a new vial. DMAT solution: DMAT (26 mg) to a new vial. Then, 5.0 ml of degassed water and 4 drops of 0.05 M NaOH was added to each vial. The solutions was stirred at 25° C. for 40 minutes. Nine ampoules (10 ml volume) were numbered from 1 to 9. BMEDA (1.0 ml) was added to ampoule No. 1. BMEDA (0.5 ml) and BT (0.5 ml) were added to ampoule No. 2. BMEDA (0.5 ml) and DMAT (50 µl) were added to ampoule No. 3. MES (1.0 ml) was added to ampoule No. 4. MES (0.5 ml) and BT (0.5 ml) were added to ampoule No. 5. MES (0.5 ml) and DMAT (50 µl) were added to ampoule No. 6. MEE (1.0 ml) was added to ampoule No. 7. MEE (0.5 ml) and BT (0.5 ml) were added to ampoule No. 8. MEE (0.5 ml) and DMAT (50 µl) were added to ampoule No. 9. After preparation, the "SXS/S" solution was labeled with $^{99m}$Tc by adding 0.20 ml of $^{99m}$Tc-glucoheptonate to each vial. After adjusting the pH to 8.0, the mixture was stirred at 25° C. for 25 min. The labeling efficiency of the $^{99m}$Tc-"SXS/S" was determined using ITLC eluted in methanol, paper chromatography eluted in methanol and paper chromatography eluted in saline.

$^{99m}$Tc-Liposome Labeling Using Various Kinds of $^{99m}$Tc-"SXS/S" Complexes For liposome labeling, an aliquot (0.60 ml) of $^{99m}$Tc-"SXS/S" 0.2 ml of 400 nm liposomes encapsulating cysteine or $(NH_4)_2SO_4$ and stirred at 25° C. for 2 hours. The labeling efficiency was determined from the $^{99m}$Tc-activity associated with the $^{99m}$Tc-liposomes before and after centrifugation.

Synthesis of $^{186}$Re-"SXS/S" Complexes

This description is for labeling $^{186}$Re with various kinds of SXS ligands and S ligands described above to produce various kinds of $^{186}$Re-"SXS/S" complexes for liposome labeling. First, a 0.17 M glucoheptonate-0.1 M acetate solution was prepared and the pH adjusted to 5.0 with 5 M NaOH. Then, nine ampoules (10 ml volume) were numbered from 1 to 9. BMEDA (2.0 µl) was added to ampoule No. 1. BMEDA (1.0 µl) and BT (0.5 µl) were added to ampoule No. 2. BMEDA (1.0 µl) and DMAT (5.2 mg/ml solution, 130 µl) were added to ampoule No. 3. MES (1.2 µl) was added to ampoule No. 4. MES (0.6 µl) and BT (0.5 µl) were added to ampoule No. 5. MES (0.6 µl) and DMAT (5.2 mg/ml solution, 130 µl) were added to ampoule No. 6. MEE (1.2 µl) was added to ampoule No. 7. MEE (0.58 µl) and BT (0.5 µl) were added to ampoule No. 8. MEE (0.58 µl) and DMAT (5.2 mg/ml solution, 130 µl) were added to ampoule No. 9. Then, 1.0 ml of the glucoheptonate-acetate solution was added to each ampoule. After flushing the "SXS/S"-glucoheptonate-acetate solution with $N_2$ gas for 20 min, the vial was sealed. The solution was stirred at 25° C. for 40 min. Next, 30 mg of $SnCl_2.2H_2O$ was dissolved by adding with 2 drops of concentrated HCl in a new vial and 2.0 ml of sterile water added.

To prepare the $^{186}$Re-"SXS/S" solution, 1.0 ml of "SXS/S" solution was transferred to a new vial and 140 µl of freshly prepared $SnCl_2.2H_2O$ was added. After flushing the "SXS/S" solution with $N_2$ gas, 2 mCi (74 MBq) of aluminum perrhenate $^{186}$Re—Al(ReO$_4$)$_3$ (~3.0 μg Re), purchased from the Missouri University Research Reactor (Columbia, Mo.), was added. The vial was sealed and heated in a 80° C. water bath for 1 hour. The labeling efficiency of the $^{186}$Re-"SXS/S" complexes were checked by instant thin layer chromatography with either acetone or saline as the eluent.

$^{186}$Re-Liposome Labeling Using Various Kinds of $^{186}$Re-"SXS/S" Complexes For liposome labeling, the pH of the $^{186}$Re-"SXS/S" solution was adjusted to 7.0. Then, 0.20 ml of 400 nm liposomes encapsulating cysteine or (NH$_4$)$_2$SO$_4$ was mixed with 0.6 ml of the $^{186}$Re-"SXS/S" solution, and incubated at 37° C. for 1 hour. The labeling efficiency was determined from the $^{186}$Re-activity associated with the $^{186}$Re-liposomes before and after centrifugation.

Figure 13:
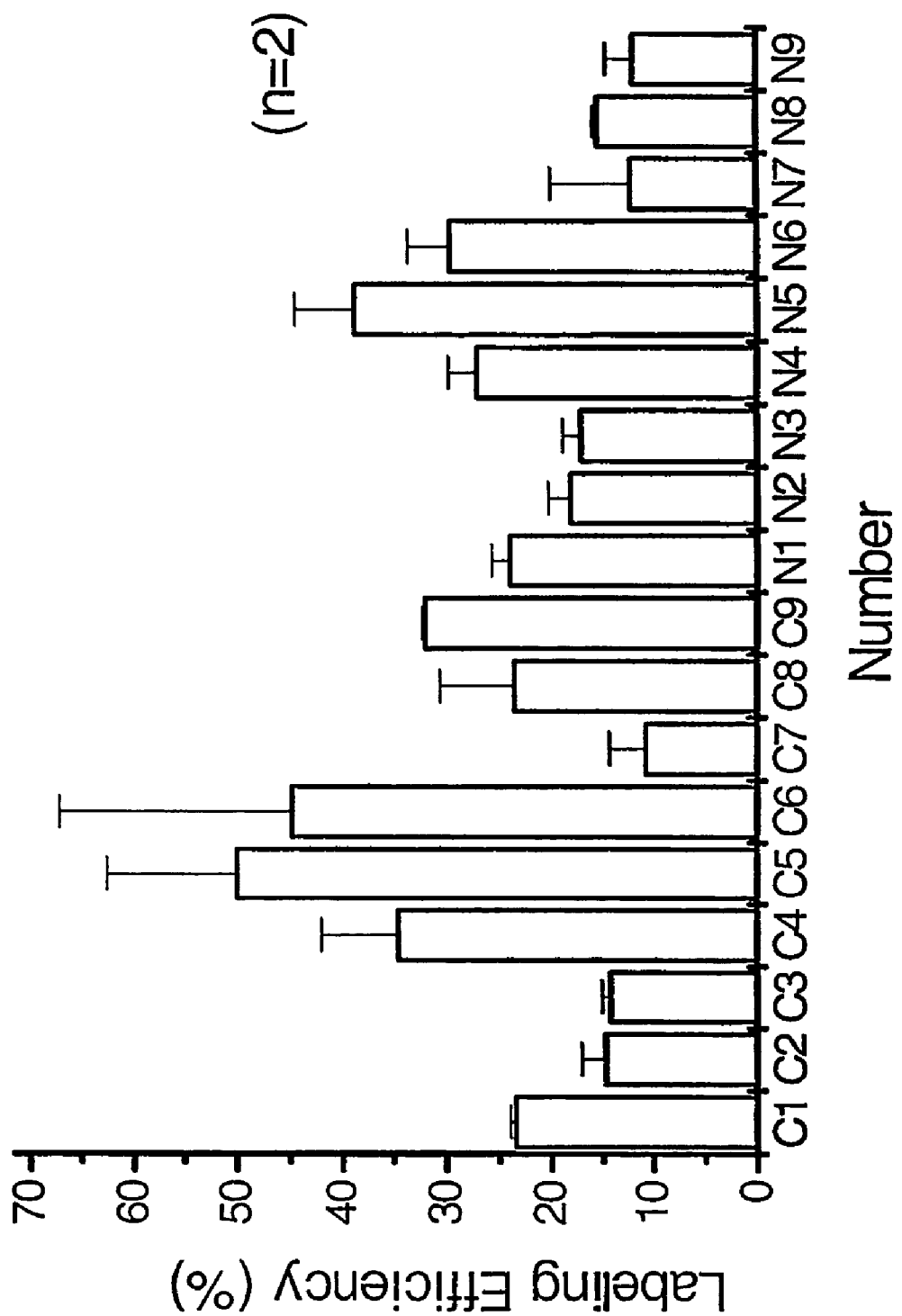
FIG. 13 shows the labeling efficiency of $^{99m}$Tc400 nm cysteine liposomes (C1-C9) and $^{99m}$Tc-400 nm $(NH_4)_2SO_4$ liposomes (N1-N9) using various kinds of $^{99m}$Tc-"SXS/S" complexes. C1 and N1 are $^{99m}$Tc-liposomes labeled with $^{99m}$Tc-"BMEDA". C2 and N2 are $^{99m}$Tc-liposomes labeled with $^{99m}$Tc-"BMEDA+BT". C3 and N3 are $^{99m}$Tc-liposomes labeled with $^{99m}$Tc-"BMEDA+DMAT". C4 and N4 are $^{99m}$Tc-liposomes labeled with $^{99m}$Tc-"MES". C5 and N5 are $^{99m}$Tc-liposomes labeled with $^{99m}$Tc-"MES+BT". C6 and N6 are $^{99m}$Tc-liposomes labeled with $^{99m}$Tc-"MES+DMAT". C7 and N7 are $^{99m}$Tc-liposomes labeled with $^{99m}$Tc-"MEE". C8 and N8 are $^{99m}$Tc-liposomes labeled with $^{99m}$Tc-"MEE+BT". C9 and N9 are $^{99m}$Tc-liposomes labeled with $^{99m}$Tc-"MEE+DMAT". (BMEDA: N,N-bis(2-mercaptoethyl) N',N'-diethylethylenediamine. MES: 2-mercaptoethyl sulfide. MEE: 2-mercaptoethyl ether. BT: benzenethiol. DMAT: 2-(dimethylamino) ethanethiol.)

Labeling Efficiency and In Vitro Stability of $^{99m}$Tc-Liposomes Labeled with Various Kinds of $^{99m}$Tc-"SXS/S" Complexes The labeling efficiencies of $^{99m}$Tc-cysteine liposomes or $^{99m}$Tc-(NH$_4$)$_2$SO$_4$ liposomes labeled with various kinds of $^{99m}$Tc-"SXS/S" complexes are shown in FIG. 13. The labeling efficiency of $^{99m}$Tc-cysteine liposomes was from 10.4% to 49.0% (n=2) depending on $^{99m}$Tc-"SXS/S" complex used. The labeling efficiency of $^{99m}$Tc-(NH$_4$)$_2$SO$_4$ liposomes was from 11.2% to 37.7% (n=2) depending on $^{99m}$Tc-"SXS/S" complex used.

Figure 14:
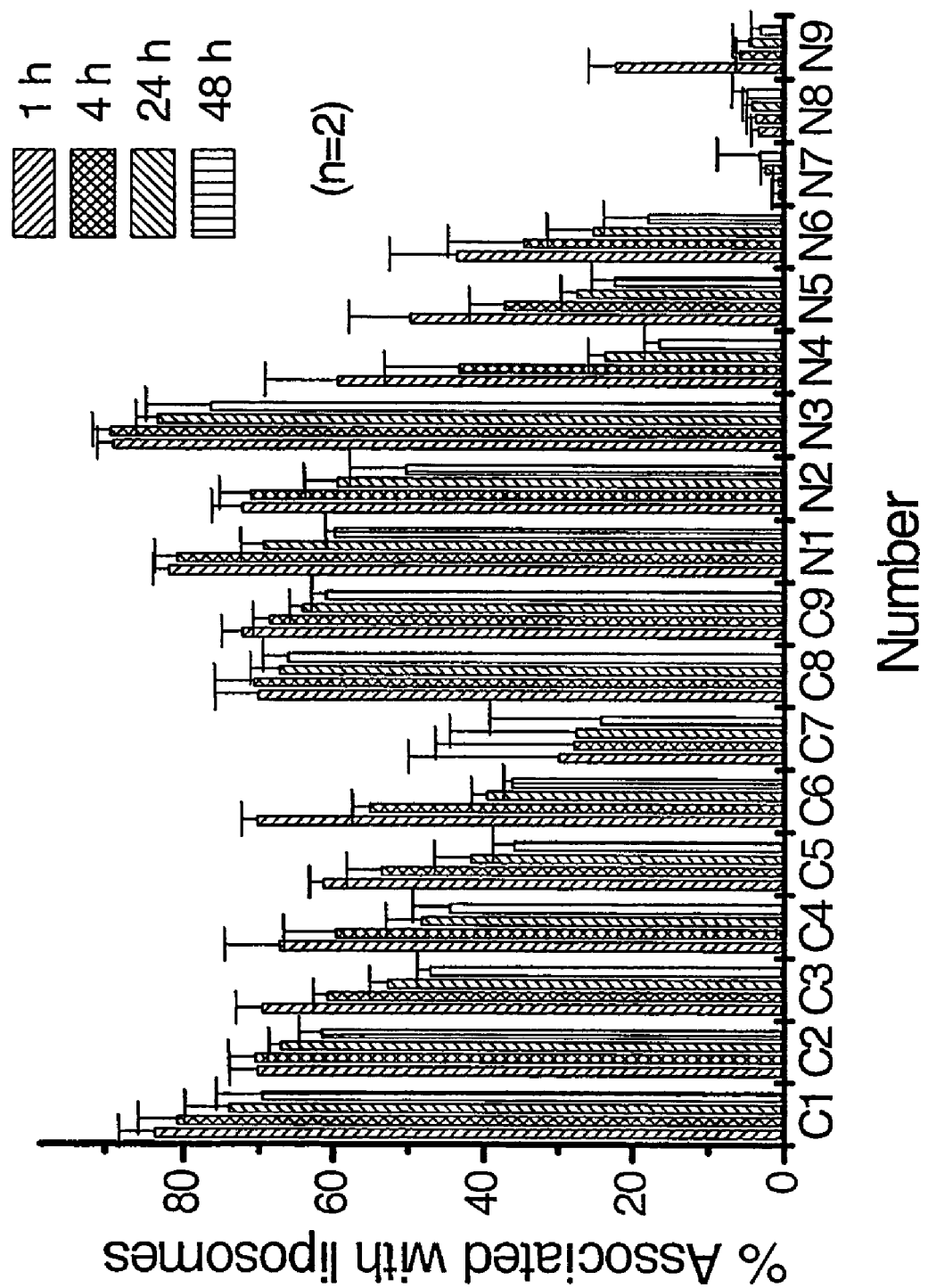
FIG. 14 shows the in vitro labeling stability (per cent of $^{99m}$Tc retained with liposomes) of $^{99m}$Tc400 nm liposomes incubated with 50% FBS-PBS solution at 37° C. at 1 h, 4 h, 24 h and 48 h. Before the in vitro labeling stability studies, the $^{99m}$Tc-liposomes were separated by centrifugation. The $^{99m}$Tc-liposomes are numbered in the same manner as described for FIG. 13.

The in vitro labeling stabilities of $^{99m}$Tc-cysteine liposomes or $^{99m}$Tc-(NH$_4$)$_2$SO$_4$ liposomes labeled with various kinds of $^{99m}$Tc-"SXS/S" complexes are shown in FIG. 14. Both $^{99m}$Tc-cysteine liposomes labeled with $^{99m}$Tc-"BMEDA" or with $^{99m}$Tc-"BMEDA+BT" and $^{99m}$Tc-(NH$_4$)$_2$SO$_4$ liposomes labeled with $^{99m}$Tc-"BMEDA" or with $^{99m}$Tc-"BMEDA+DMAT" had the best in vitro labeling stability with 67.0-83.1% of activity associated with liposomes at 24 h depending on $^{99m}$Tc-"SXS/S" complex used and with 59.7-76.5% at 48 h.

Figure 15:
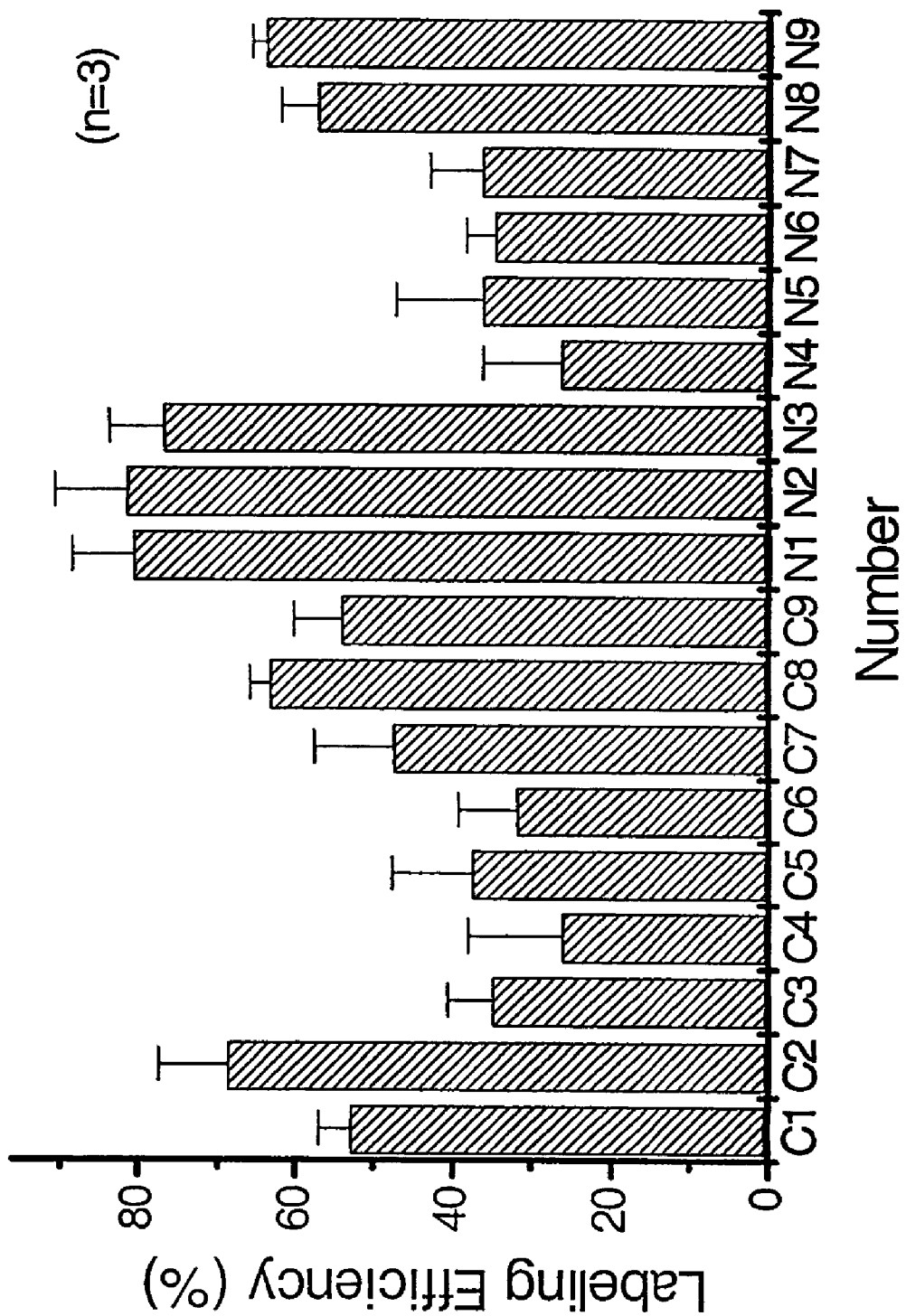
FIG. 15 shows the labeling efficiency of $^{186}$Re-400 nm cysteine liposomes (C1-C9) and $^{186}$Re-400 nm $(NH_4)_2SO_4$ liposomes (N1-N9) using various kinds of $^{186}$Re-"SXS/S" complexes. C1 and N1 are $^{186}$Re-liposomes labeled with $^{186}$Re-"BMEDA". C2 and N2 are $^{186}$Re-liposomes labeled with $^{186}$Re-"BMEDA+BT". C3 and N3 are $^{186}$Re-liposomes labeled with $^{186}$Re-"BMEDA+DMAT". C4 and N4 are $^{186}$Re-liposomes labeled with $^{186}$Re-"MES". C5 and N5 are $^{186}$Re-liposomes labeled with $^{186}$Re-"MES+BT". C6 and N6 are $^{186}$Re-liposomes labeled with $^{186}$Re-"MES+DMAT". C7 and N7 are $^{186}$Re-liposomes labeled with $^{186}$Re-"MEE". C8 and N8 are $^{186}$Re-liposomes labeled with $^{186}$Re-"MEE+BT". C9 and N9 are $^{186}$Re-liposomes labeled with $^{186}$Re-"MEE+DMAT" (BMEDA: N,N-bis(2-mercaptoethyl) N',N'-diethylethylenediamine. MES: 2-mercaptoethyl sulfide. MEE: 2-mercaptoethyl ether. BT: benzenethiol. DMAT: 2-(dimethylamino) ethanethiol.).

Labeling Efficiency and In Vitro Stability of $^{186}$Re-Liposomes Labeled with Various Kinds of $^{186}$Re-"SXS/S" Complexes The labeling efficiencies of $^{186}$Re-cysteine liposomes or $^{186}$Re—(NH$_4$)$_2$SO$_4$ liposomes labeled with various kinds of $^{186}$Re-"SXS/S" complexes are shown in FIG. 15. The labeling efficiency of $^{186}$Re-cysteine liposomes was from 26.1% to 68.7% (n=3) depending on $^{186}$Re-"SXS/S" complex used. The labeling efficiency of $^{186}$Re—(NH$_4$)$_2$SO$_4$ liposomes was from 26.2% to 81.3% (n=3) depending on $^{186}$Re-"SXS/S" complex used.

Figure 16:
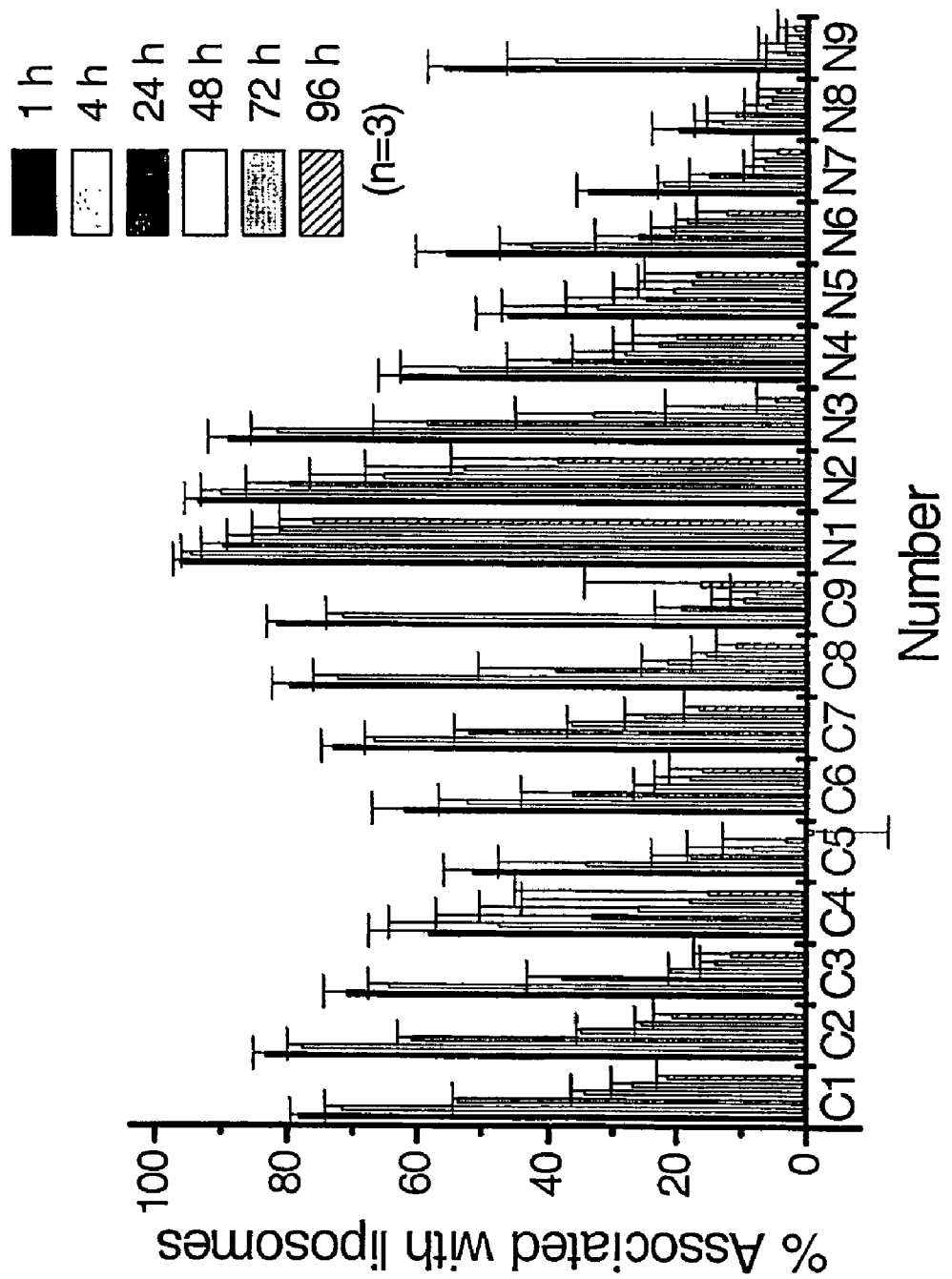
FIG. 16 shows the in vitro labeling stability (per cent of $^{186}$Re retained with liposomes) of $^{186}$Re-400 nm liposomes incubated with 50% FBS-PBS solution at 37° C. at 1 h, 4 h, 24 h and 48 h. Before the in vitro labeling stability studies, the $^{186}$Re-liposomes were separated by centrifugation. The $^{186}$Re-liposomes are numbered in the same manner as described for FIG. 15.

The in vitro labeling stabilities of $^{186}$Re-cysteine liposomes or $^{186}$Re—(NH$_4$)$_2$SO$_4$ liposomes labeled with various kinds of $^{186}$Re-"SXS/S" complexes are shown in FIG. 16. $^{186}$Re—(NH$_4$)$_2$SO$_4$ liposomes labeled with $^{186}$Re-"BMEDA" had the best in vitro labeling stability with 96.1±1.1% of activity associated with liposomes at 1 h, 94.4±1.5% at 4 h, 89.8±3.1% at 24 h, 85.4±3.9% at 48 h, 80.9±4.5% at 72 h, 76.2±5.1% at 96 h (n=3).

$^{99m}$Tc-Doxil® Labeling Using $^{99m}$Tc-"BMEDA"

Doxil® is a commercially available preparation of liposomes encapsulating doxorubicin. For Doxil® labeling, an aliquot (15 mCi) (0.50 ml) of $^{99m}$Tc-"BMEDA" was added to 0.50 ml of Doxil® and stirred at 25° C. for 2 hours. The labeling efficiency was determined from the $^{99m}$Tc-activity associated with Doxil® before and after separation using Sephadex G-25 column.

Labeling Efficiency and In Vitro Stability of $^{99m}$Tc-Doxil® Labeled with $^{99m}$Tc-"BMEDA"

Figure 17:
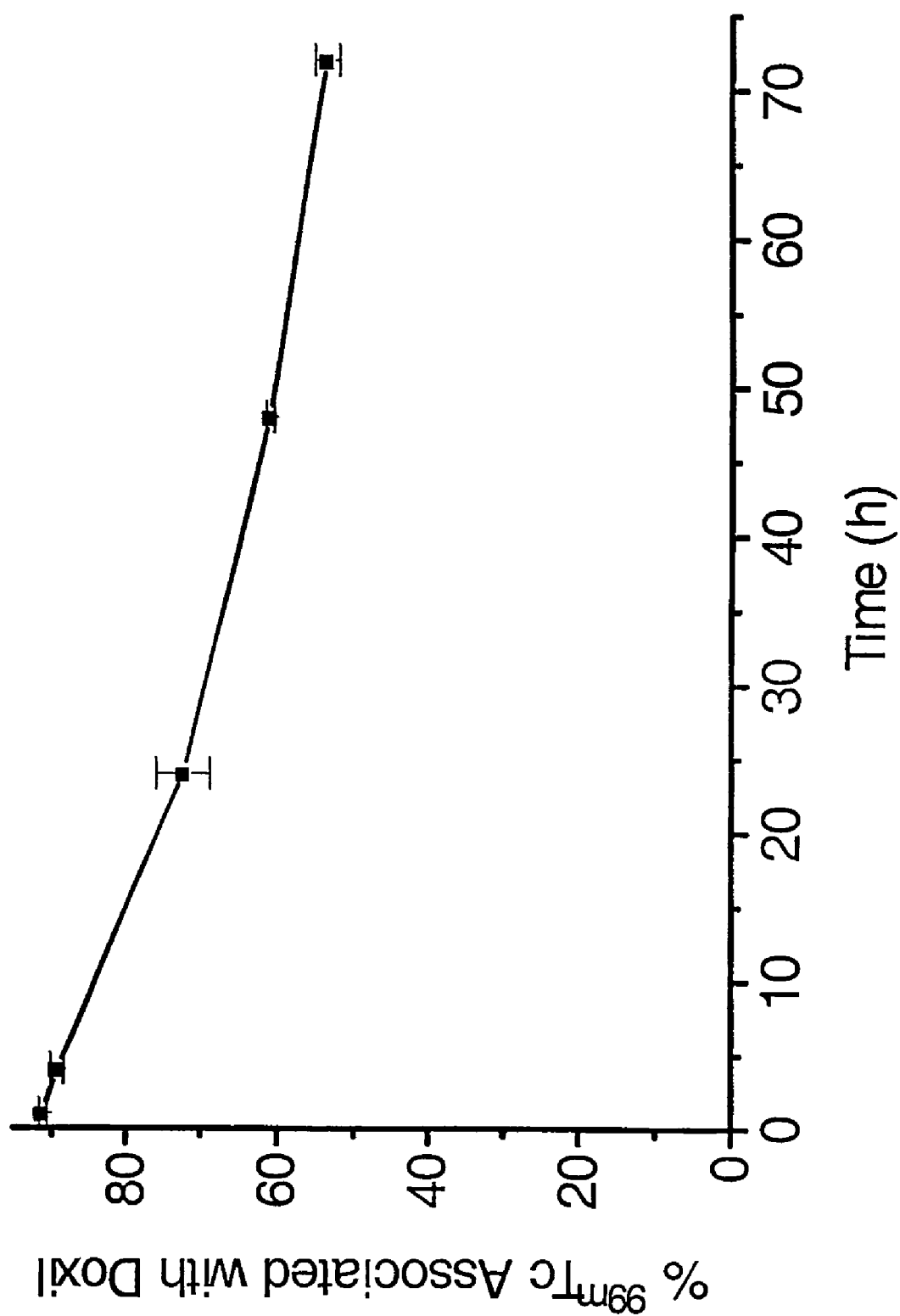
FIG. 17 shows the in vitro labeling stability (per cent of $^{99m}$Tc retained with Doxil®) of $^{99m}$Tc-Doxil® labeled with $^{99m}$Tc-"BMEDA" incubated with 50% FBS-PBS solution at 37° C. at 1 h, 4 h, 24 h, 48 h and 72 h. Before the in vitro labeling stability studies, the $^{99m}$Tc-Doxil® was separated using Sephadex G-25 column chromatography. The per cent of $^{99m}$Tc retained with Doxil® was determined using Bio-Gel A-15 m gel spin column.

The labeling efficiency of $^{99m}$Tc-Doxil® was 70.8±0.6% (n=3). The in vitro labeling stability of $^{99m}$Tc-Doxil® is shown in FIG. 17. There was 89.4±0.5% of $^{99m}$Tc associated with Doxil® after we stored the separated $^{99m}$Tc-Doxil® at 25° C. for 24 h. $^{99m}$Tc-Doxil® had good in vitro labeling stability with 72.3±3.6% (n=3) of activity associated with Doxil® at 24 h incubated with 50% FBS-PBS solution at 37° C.

Throughout this application, various publications are references The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having the formula I

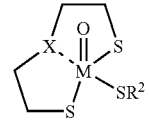

wherein
M is $^{99m}$Tc, $^{186}$Re or $^{188}$Re;
X is NR$^1$ wherein R$^1$ is CH$_2$CH$_2$NEt$_2$ or CH$_2$CH$_2$CH$_2$CH$_3$; and
R$^2$ is CH$_2$CH$_2$N(CH$_2$CH$_2$SH)(CH$_2$CH$_2$NEt$_2$) or CH$_2$CH$_2$N(CH$_2$CH$_2$SH)(CH$_2$CH$_2$CH$_2$CH$_3$).

2. The compound of claim 1, wherein R$^1$ is CH$_2$CH$_2$NEt$_2$ and R$^2$ is CH$_2$CH$_2$N(CH$_2$CH$_2$SH)(CH$_2$CH$_2$NEt$_2$).

3. The compound of claim 1, wherein R$^1$ is CH$_2$CH$_2$CH$_2$CH$_3$ and R$^2$ is CH$_2$CH$_2$N(CH$_2$CH$_2$SH) (CH$_2$CH$_2$CH$_2$CH$_3$).

4. A radiolabeled liposome comprising a liposome and a compound having the formula I

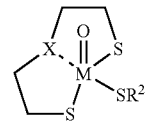

wherein
M is $^{99m}$Tc, $^{186}$Re, or $^{188}$R;
X is NR$^1$ wherein R$^1$ is CH$_2$CH$_2$NEt$_2$ or CH$_2$CH$_2$CH$_2$CH$_3$; and
R$^2$ is CH$_2$CH$_2$N(CH$_2$CH$_2$SH)(CH$_2$CH$_2$NEt$_2$) or CH$_2$CH$_2$N(CH$_2$CH$_2$SH)(CH$_2$CH$_2$CH$_2$CH$_3$)
wherein the compound is incorporated or attached to the liposome.

5. The radiolabeled liposome of claim 4, wherein the liposome further comprises a drug that is incorporated within the liposome.

6. The radiolabeled liposome of claim 5, wherein the drug is a compound comprising at least one thiol group.

7. The radiolabled liposome of claim 6, wherein the drug reacts with the compound having the formula I.

8. The radiolabeled liposome of claim 5, wherein the drug comprises glutathione, cysteine, N-acetyl cysteine, 2-mercaptosuccinic acid, 2,3-dimercaptosuccinic acid, captopril or a combination thereof.

9. The radiolabeled liposome of claim 4, wherein the liposome comprises a lipid.

10. The radiolabeled liposome of claim 4, wherein the liposome comprises a phospholipid.

11. The radiolabeled liposome of claim 4, wherein the liposome comprises a cholesterol or a cholesterol analogue.

12. The radiolabeled liposome of claim 10, wherein the liposome comprises distearoyl phosphatidylcholine.

13. The radiolabeled liposome of claim 4, wherein the amount of radionuclide attached or incorporated into the liposome is from about 0.01 mCi to about 400 mCi per 50 mg of lipid that is used to prepare the liposome.

14. The radiolabeled liposome of claim 4, wherein the liposome further comprises a chemotherapeutic agent, an antibiotic agent or a treatment molecule, wherein the chemotherapeutic agent, the antibiotic agent, or the treatment molecule is incorporated or attached to the liposome.

15. A method of making a radiolabeled liposome, comprising mixing
   a. a liposome having an outer space and an inner volume, wherein the pH of the inner volume of the liposome is less than the pH of the outer space of the liposome, with
   b. a compound having the formula I

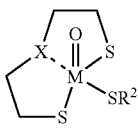

wherein

M is $^{99m}$Tc, $^{186}$Re, or $^{188}$Re;

X is $NR^1$ wherein $R^1$ is $CH_2CH_2NEt_2$ or $CH_2CH_2CH_2CH_3$; and $R^2$ is $CH_2CH_2N(CH_2CH_2SH)(CH_2CH_2NEt_2)$ or $CH_2CH_2N(CH_2CH_2SH)(CH_2CH_2CH_2CH_3)$, wherein after components (a) and (b) are mixed, the compound is incorporated or attached to the liposome.

16. The method of claim 15, wherein the pH of the inner volume of the liposome is acidic and the pH of the outer space of the liposome is neutral, basic, or a physiological pH.

17. The method of claim 15, wherein the inner volume of the liposome contains a compound comprising at least one amine group or at least one carboxyl group.

18. The method of claim 15, wherein the inner volume of the liposome contains ammonium sulfate.

19. The method of claim 15, wherein the pH of the inner volume is from about 4 to about 7 and the pH of the outer space is from about 6 to about 7.4.

20. The method of claim 15, wherein after the liposome and the compound having the formula I are mixed, the radiolabeled liposome is incubated at from 25° C. to 37° C. for 0.5 to 2 hours.

21. The radiolabeled liposome produced by the method of claim 15.

22. A method of making a radiolabeled liposome, comprising mixing
   a. a liposome having an outer space and an inner volume, wherein a drug comprising at least one thiol group is incorporated within the inner volume of the liposome, with
   b. a compound having the formula I

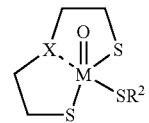

wherein

M is $^{99m}$Tc, $^{186}$Re, or $^{188}$Re;

X is $NR^1$ wherein $R^1$ is $CH_2CH_2NEt_2$ or $CH_2CH_2CH_2CH_3$; and $R^2$ is $CH_2CH_2N(CH_2CH_2SH)(CH_2CH_2NEt_2)$ or $CH_2CH_2N(CH_2CH_2SH)(CH_2CH_2CH_2CH_3)$, wherein after components (a) and (b) are mixed, the compound is incorporated into the liposome.

23. The method of claim 22, wherein the drug reacts with the compound having the formula I.

24. The method of claim 22, wherein the drug comprises glutathione, cysteine, N-acetyl cysteine, or a combination thereof.

25. The method of claim 22, wherein after the liposome and the compound having the formula I are mixed, the radiolabeled liposome is incubated at from 25° C. to 37° C. for 0.5 to 2 hours.

26. A radiolabeled liposome made by the method of claim 22.

27. A kit comprising
   a. a liposome having an outer space and an inner volume, wherein the pH of the inner volume of the liposome is less than the pH of the outer space of the liposome, and
   b. a compound having the formula I

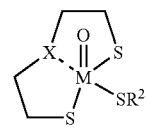

wherein

M is $^{99m}$Tc, $^{186}$Re, or $^{188}$Re;

X is $NR^1$ wherein $R^1$ is $CH_2CH_2NEt_2$ or $CH_2CH_2CH_2CH_3$; and $R^2$ is $CH_2CH_2N(CH_2CH_2SH)(CH_2CH_2NEt_2)$ or $CH_2CH_2N(CH_2CH_2SH)(CH_2CH_2CH_2CH_3)$.

28. A kit comprising
   a. a liposome having an outer space and an inner volume, wherein a drug comprising at least one thiol group is incorporated within the inner volume of the liposome, and b. a compound having the formula I

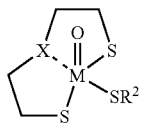

wherein
M is $^{99m}$Tc, $^{186}$Re, or $^{188}$Re;
X is $NR^1$ wherein $R^1$ is $CH_2CH_2NEt_2$ or $CH_2CH_2CH_2CH_3$; and
$R^2$ is $CH_2CH_2N(CH_2CH_2SH)(CH_2CH_2NEt_2)$ or $CH_2CH_2N(CH_2CH_2SH)(CH_2CH_2CH_2CH_3)$.

29. The radiolabeled liposome of claim 4, wherein $R^1$ is $CH_2CH_2NEt_2$ and $R^2$ is $CH_2CH_2N(CH_2CH_2SH)(CH_2CH_2NEt_2)$.

30. The method of claim 15, wherein $R^1$ is $CH_2CH_2NEt_2$ and $R^2$ is $CH_2CH_2N(CH_2CH_2SH)(CH_2CH_2NEt_2)$.

31. The method of claim 22, wherein $R^1$ is $CH_2CH_2NEt_2$ and $R^2$ is $CH_2CH_2N(CH_2CH_2SH)(CH_2CH_2NEt_2)$.

32. The method of claim 26, wherein $R^1$ is $CH_2CH_2NEt_2$ and $R^2$ is $CH_2CH_2N(CH_2CH_2SH)(CH_2CH_2NEt_2)$.

33. The kit of claim 27, wherein $R^1$ is $CH_2CH_2NEt_2$ and $R^2$ is $CH_2CH_2N(CH_2CH_2SH)(CH_2CH_2NEt_2)$.

34. The kit of claim 28, wherein $R^1$ is $CH_2CH_2NEt_2$ and $R^2$ is $CH_2CH_2N(CH_2CH_2SH)(CH_2CH_2NEt_2)$.

\* \* \* \* \*

UNITED STATES PATENT AND TRADEMARK OFFICE
CERTIFICATE OF CORRECTION

| | |
|---|---|
| PATENT NO. | : 7,718,160 B2 |
| APPLICATION NO. | : 10/518872 |
| DATED | : May 18, 2010 |
| INVENTOR(S) | : Ande Bao et al. |

It is certified that error appears in the above-identified patent and that said Letters Patent is hereby corrected as shown below:

In claim 7, column 27, line 3, delete "radiolabled" and insert --radiolabeled-- therefor.

In claim 12, column 27, line 16, delete "phosphatidyicholine" and insert --phosphatidylcholine-- therefor.

Signed and Sealed this

Seventh Day of September, 2010

David J. Kappos
*Director of the United States Patent and Trademark Office*